US011571407B2

(12) United States Patent
Farrera-Sinfreu et al.

(10) Patent No.: US 11,571,407 B2
(45) Date of Patent: Feb. 7, 2023

(54) BICALUTAMIDE ANALOGS OR (S)-BICALUTAMIDE AS EXOCYTOSIS ACTIVATING COMPOUNDS FOR USE IN THE TREATMENT OF A LYSOSOMAL STORAGE DISORDER OR GLYCOGENOSIS

(71) Applicant: BCN PEPTIDES, S.A., Sant Quinti De Mediona Barcelona (ES)

(72) Inventors: Josep Farrera-Sinfreu, Tírvia (ES); Leslie Matalonga Borrel, Barcelona (ES); Laura Gort Mas, Balenyà (ES); Roberto Pascual Martínez, Alicante (ES); Antonio Ferrer Montiel, Alicante (ES); Antonia Ribes Rubió, Esplugues De Llobregat (ES); Berta Ponsati Obiols, Barcelona (ES)

(73) Assignee: BCN PEPTIDES, S.A., Sant Quinti de Mediona (ES)

( * ) Notice: Subject to any disclaimer, the term of this patent is extended or adjusted under 35 U.S.C. 154(b) by 0 days.

(21) Appl. No.: 15/102,358

(22) PCT Filed: Dec. 19, 2014

(86) PCT No.: PCT/EP2014/078745
§ 371 (c)(1),
(2) Date: Jun. 7, 2016

(87) PCT Pub. No.: WO2015/097088
PCT Pub. Date: Jul. 2, 2015

(65) Prior Publication Data
US 2016/0317489 A1 Nov. 3, 2016

(30) Foreign Application Priority Data
Dec. 23, 2013 (EP) ..................................... 13382541

(51) Int. Cl.
*A61K 31/277* (2006.01)
*A61K 31/167* (2006.01)
*A61K 47/42* (2017.01)
*G01N 33/566* (2006.01)

(52) U.S. Cl.
CPC .......... *A61K 31/277* (2013.01); *A61K 31/167* (2013.01); *A61K 47/42* (2013.01); *G01N 33/566* (2013.01); *G01N 2333/70596* (2013.01); *G01N 2800/7066* (2013.01)

(58) Field of Classification Search
CPC .................................................. A61K 31/277
See application file for complete search history.

(56) References Cited

U.S. PATENT DOCUMENTS

| 6,071,957 A | 6/2000 | Miller et al. |
| 2008/0076828 A1 | 3/2008 | Dalton et al. |
| 2011/0217288 A1 | 9/2011 | Shen et al. |
| 2013/0023488 A1 | 1/2013 | Wu |

FOREIGN PATENT DOCUMENTS

| WO | 9853826 A1 | 12/1998 |
| WO | 9855153 A1 | 12/1998 |
| WO | 9216310 A1 | 2/2002 |
| WO | WO-2008/008433 A2 | 1/2008 |
| WO | 2010015816 A2 | 2/2010 |
| WO | 2011119544 A1 | 9/2011 |
| WO | WO-2011/109448 A1 | 9/2011 |
| WO | 2012139093 A2 | 10/2012 |

OTHER PUBLICATIONS

International Search Report and Written Opinion of the ISA, ISA/EP, Rijswijk, NL, dated Feb. 5, 2015.
Annunziata et al.: Study of Influence of Sex and Age on human serum lysosomal enzymes by using 4-methylumbelliferyl substiates; Clinica Chimica Acta, 90, 101-106, 1978.
Barbosa et al.; Improved and simple micro assay for sulfated glycosaminoglycans quantification in biological extracts and its use in skin and muscle tissue studies; Glycobiology vol. 13, No. 9, pp. 647-653, 2003.
Berge et al.; Pharmaceutical Salts; J. Pharm Sciences; vol. 66, No. 1,1977.
Bidou et al.; Premature stop condons involved in muscular dystrophies show a broad spectrum of readthrough efficiencies in response to gentamicin treatment; Gene Therapy 2004, 11, 619-627.
Boyd et al.; Pharmacological Chaperones as Therapeutics for Lysomsomal Storage Diseases; J Medicinal Chem; 2013; 56, 2705-2725.
Chen et al.; Cyclodextrin induces calcium-dependent lysosomal exocytosis; Plos One, Nov. 2010, v5, Issue 11,e15054.
Cockshott; Clinical Pharmacokinetics and Metabolism; Clin Pharm 2004: 43(13), 855-878.
Floquet et al.; Allele-specific therapy: suppression of nonsense mutations by readthrough inducer; Med. Sci, (Paris) 2012; 28(2), 193-199; English Summary, p. 198-199.
Haurigot et al.; Whole body correction of mucopolysaccharidosis 11 IA by intracerebrospinal fluid gene therapy; J Clinical Investigation; V 123; No. 8, Aug. 2013.
Helip-Wooley et al.; Expression of CTNS Alleles: Subcellular Localization and Aminoglycoside Correction in Vitro; Mol. Genetics and Metabolism; 75, 128-133, 2002.

(Continued)

*Primary Examiner* — Yong S. Chong
(74) *Attorney, Agent, or Firm* — Harness, Dickey & Pierce, P.L.C.

(57) ABSTRACT

The invention provides a therapy for lysosomal storage diseases and glycogenosis by treatment with compounds that promote exocytosis, preferably lysosomal exocytosis. The treatment of cells from patients affected by different lysosomal storage disorders with exocytosis activating compounds leads to a decrease in the accumulation of toxic substrate in the lysosomes, thus allowing the treatment, prevention and relief of the symptoms of many lysosomal storage disorders.

20 Claims, 1 Drawing Sheet
(1 of 1 Drawing Sheet(s) Filed in Color)

(56) References Cited

OTHER PUBLICATIONS

Hers; The role of lysosomes in the pathogeny of storage diseases; Biochime, 1972, 54; 753-756.
Moss; Basic Terminology of Stereochemistry; Pure & Appl. Chem, V 68, No. 12, pp. 2193-2222; 1996.
Keeling et al.; Gentamicin-mediated suppression of Hureler syndrome stop mutations restores a low level of a-L-iduroniadase activity and reduces lysosomal glycosaminoglycan accumulation; Human molecular genetics, 2001, v 10, No. 3, 291-299.
Kuzmaik et al.; Applying nonsense-mediated mRNA decay research to the clinic: progress and challenges; Trends in Molecular Medicine; v 12, No. 7, Jul. 2006.
Medina et al.; Transcriptional Activation of Lysosomal Exocytosis Promotes Cellular Clearance; D. Cell 21, 421-430, Sep. 12, 2011.
Mukherjee et al.; Enantioselective Binding of Casodex to the Androgen Receptor; Xenobiotica; 1996, v 26, No. 2, 117-122.
Nudelman et al.; Repairing faulty genes by aminoglycosides: Development of new derivatives of geneticin (G418) with enhanced suppression of diseases-causing nonsense mutations; Bioorganic & Med Chem; 18, 2010, 3735-3746.
Parenti; Treating Lysosomal Storage Diseases with Pharmacological Chaperones: from Concept to Clinics; EMBO Molecular Med. 1, 268-279, 2009.
Gregory M. Pastores; Lysosomal Storage Disorders: Principles and Practice; World Scientific Publishing Co. Pte. Ltd.; 2010.
Rowe et al.; Handbook of Pharmaceutical Excipients, 6th Edition; Pharmaceutical Press 2009.
Charles R. Scriver; Human Genetics: Lessons from Quebec Populations; Annu Rev. Genomics Hum. Genet. 2001, 2:69-101.
Shen et al.; The role of androgen receptor pathway in pathogensis of Fabry disease and its therapeutic implications; 2013 XP002723288.
Venil Sumantran; Cellular Chemosensitivity Assays: An Overview; Methods Mol. Biol. (2011), 731,219-236.
Tomain et al.: Gene therapy approaches for Lysosomal Storage disorders, a good model for the treatment of mendeliar diseases; Acta Paediatr. (2012), 101(7), 692-701.
Valenzano et al.; Identification and Characterization of Pharmacological Chaperones to Correct Enzyme Deficiencies iun Lysosomal Storage Disorders; Assay Drug Dev. Technol. (2011), 9(3), 213-235.
Miao Xu et al.; 8-Tocopherol Reduces Lipid Accumulation in Niemann-Pick type C1 and Wolman Cholesterol Storage Disorders; J. Biol. Chem. (2012), 287(47), 39349-39360.
He et al.; "Novel nonsteroidal ligands with high binding affinity and potent functional activity for the androgen receptor" (Eur. J Med. Chem. 2002, 37, 619-634).
Yin et al.; "Pharmacodynamics of selective androgen receptor modulators"; (J. Pharmacol. Exp. Ther. 2003, 304(3), 1334-1340).
Huang et al.; "Current status of diagnosis and treatment of lysosomal storage diseases in China"; (World J. Pediatr. 2 (4), 245-251 (2006)).
Narayanan et al.; "Development of Selective Androgen Receptor Modulators (SARMs)." Mol. Cell Endocrinol. 2018, 465, 134-142.

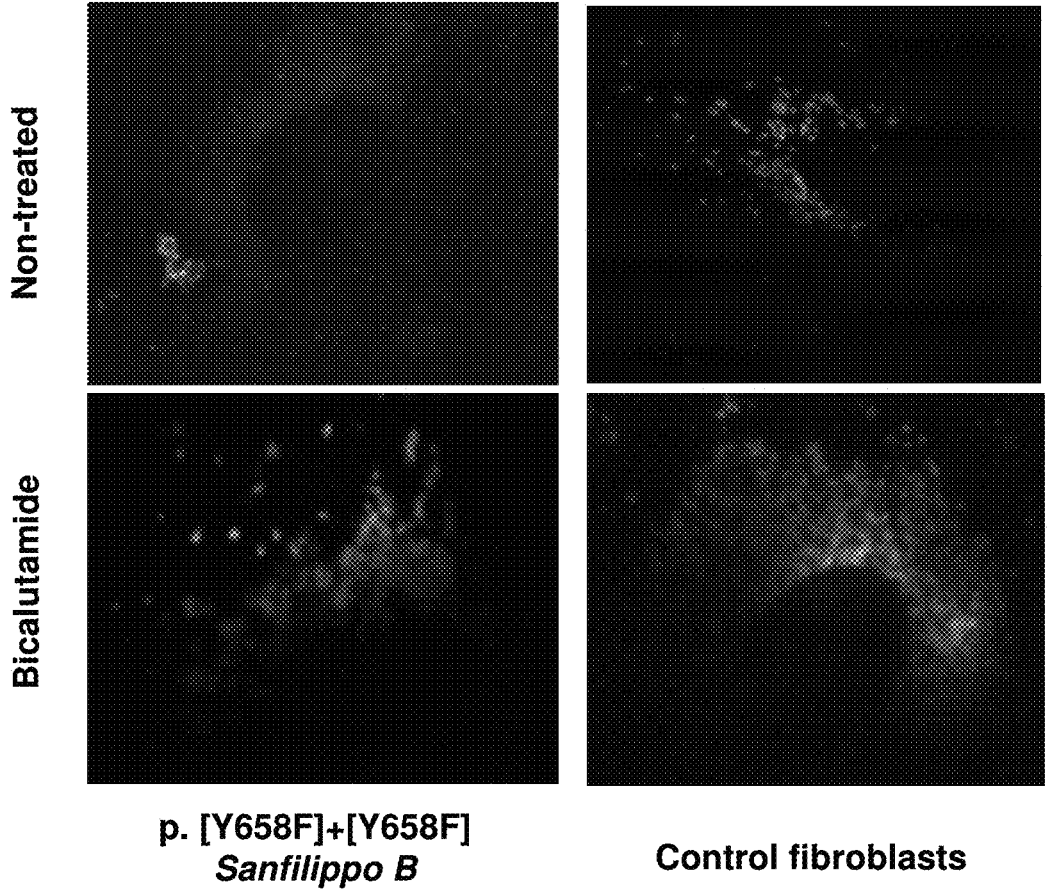

US 11,571,407 B2

BICALUTAMIDE ANALOGS OR (S)-BICALUTAMIDE AS EXOCYTOSIS ACTIVATING COMPOUNDS FOR USE IN THE TREATMENT OF A LYSOSOMAL STORAGE DISORDER OR GLYCOGENOSIS

CROSS-REFERENCE TO RELATED APPLICATIONS

This application is a 371 U.S. National Stage of International Application No. PCT/EP2014/078745, filed Dec. 19, 2014, which claims the benefit of and priority to European Patent Application No. 13382541.4, filed Dec. 23, 2013. The entire disclosures of the above applications are incorporated herein by reference.

FIELD OF THE INVENTION

The present invention is within the area of biomedical chemistry. In particular, the invention relates to the field of lysosomal storage diseases and glycogenosis, and more specifically to their pharmacological treatment with molecules that promote exocytosis.

BACKGROUND OF THE INVENTION

Lysosomal storage diseases (LSDs) and glycogenosis are genetic disorders involving the accumulation of macromolecules in cells. In LSDs the accumulation is produced within lysosomes, as it occurs in some glycogenosis.

Lysosomal storage diseases are extensively documented, as for example in *Lysosomal Storage Disorders: Principles and Practice*, by Pastores, G. M., *World Scientific* (2009) or in *Lysosomal Storage Diseases: Early Diagnosis & New Treatments* by Rossella Parini et al., John Libbey *Eurotext* (2010).

Lysosomal storage diseases are historically classified on the basis of their storage product (sphingolipidoses and sphingolipid activator defects, mucopolysaccharidoses, glycoproteinoses and other enzymatic defects) or the nature of their molecular defect (defect in post-translational processing of lysosomal enzymes, lysosomal membrane and transport defects, neuronal lipofuscinoses and defect in lysosomes-related organelle biogenesis). There are more than 50 LSDs which are inherited in an autosomal recessive manner or X-linked. The global incidence of LSDs is approximately 1 in 5000 live births. Most of them are caused by the deficiency of a particular lysosomal hydrolytic enzyme involved in the degradation of a specific substrate leading to its toxic accumulation. In a few cases, pathologies are caused by a defective lysosomal membrane protein, defective enzyme targeting or defective function of enzyme activator [Hers H G, *The role of lysosomes in the pathogeny of storage diseases. Biochimie*. (1972), 54(5), 753-757; Scriver C R, *Human genetics: lessons from Quebec populations. Annu. Rev. Genomics Hum. Genet*. (2001), 2, 69-101; Tomanin et al., *Gene therapy approaches for lysosomal storage disorders, a good model for the treatment of mendelian diseases. Acta Paediatr*. (2012), 101(7), 692-701]. The spectrum of symptoms and phenotype variation in LSDs are of wide range, mainly due to a high allelic heterogeneity, causing serious neurodegenerative and multisystemic clinical symptoms.

Glycogenosis are inherited disorders that affect proteins involved in the synthesis or degradation of glycogen. More than 9 different types of glycogenosis have been described in accordance with the chronological order of enzymatic deficiency identification. Tissues characterized by higher amounts of glycogen, such as muscle and liver, are the most affected by these diseases. Most common symptoms are: hepatomegaly, hypoglycaemia, muscle cramps, exercise intolerance, susceptibility to fatigue, and progressive muscle weakness. Glycogenosis have variable prognosis, from mild symptoms to severe forms with early death. As it occurs in LSDs, most of the existing treatments are palliative. Different therapeutic strategies have emerged in the last years, such as: maintenance of normal blood glucose concentration by strict dietary regimens (parenteral or nasogastric nutrition) or kidney and/or liver transplantation in glycogenosis types I and III, and high carbohydrate and protein diet for glycogenosis types IV, VI and IX. However, the usefulness of these therapies is limited and no satisfactory treatments for progressive miopathy exist [Scriver C R, *Human genetics: lessons from Quebec populations. Annu. Rev. Genomics Hum. Genet*. (2001), 2, 69-101].

The lack of activity of an enzyme which is responsible of the degradation of a substrate leads to the toxic accumulation of said substrate. The mechanism by which storage materials cause a severe cascade of cellular alterations (such as, for example, altered calcium homeostasis, signalling pathways, trafficking, inflammation, and oxidative stress), is common in LSDs, but the physiopathology of these diseases is still not fully understood. However, residual enzymatic activity depends generally on the mutation and in most cases the severity of the disease correlates with the degree of the enzymatic deficiency. It is considered that a residual enzymatic activity of only 10-20% of normal values may be enough for function recovery resulting in wild type phenotype [Bidou et al, *Premature stop codons involved in muscular dystrophies show a broad spectrum of readthrough efficiencies in response to gentamicin treatment. Gene Ther.* (2004), 11(7), 619-627].

For many years, the treatment for patients suffering from these diseases mainly consisted of supportive care. More recently, new therapeutic strategies have emerged. During the 90's, haematopoietic stem cell transplantation (HSCT) began to be implemented, the first enzyme replacement therapy (ERT) was applied in 1991 for Gaucher disease, from 2000 onwards, new ERTs for more lysosomal diseases and later, substrate reduction therapy (SRT) emerged. [Parenti, *Treating lysosomal storage diseases with pharmacological chaperones: from concept to clinics. EMBO Mol Med* (2009), 1(5), 268-279]. These therapies have led to certain improvements in some of the diseases.

Haematopoietic stem cell transplantation (HSCT) is limited to particular diseases and is associated with high rates of morbidity and mortality due to rejection, toxicity, infections, secondary tumours or sequelae. The success of this therapy stems mainly from the possibility of encountering an identical donor. This therapy has been tested in several lysosomal diseases but, in most of them, little clinical benefits have been achieved; indeed, some of them showed controversial or negative results. This therapy has only been applied with some success in Mucopolysaccharidosis type I (Hurler disease), Metachromatic leukodistrophy, Krabbe disease, α-mannosidosis and Mucopolysaccharidosis type VI (Maroteaux-Lamy syndrome), among others.

Enzyme replacement therapy (ERT) is applied when an enzymatic deficiency exists. It is only available for some diseases and is limited to systemic affectation as the enzymes are unable to cross the blood-brain barrier, and therefore this therapy is not able to reverse central nervous system manifestations. Furthermore, ERT is not capable of improving bone and valve symptoms, or acting in apoptosis or inflammation. Overall, it is a well-tolerated therapy with low toxicity and moderate side effects. In return, continuous intravenous administration is required besides being a very expensive and not so effective therapy. Currently available ERT treatments exist for Gaucher, Fabry, Pompe and Mucopolysaccharidoses types I, II and VI diseases.

Substrate reduction therapy (SRT) attempts to prevent substrate accumulation and to restore the metabolic balance. This treatment is only currently available for Gaucher and Niemman-Pick type C diseases.

Limited benefits of these therapies arise because of incompatible donors, possible graft failure and because compounds are not able to cross the blood-brain barrier. These therapies are not 100% effective and in most cases only partial improvement of symptoms is observed. Therefore, there is a need of developing more effective and universal therapies, as most of these diseases have no real treatment.

Thereby, recently other potential strategies such as the use of pharmacological chaperones or compounds capable of inducing readthrough of premature termination codons (PTCs) have emerged [Kuzmiak et al, *Applying nonsense-mediated mRNA decay research to the clinic: progress and challenges. Trends Mol Med.* (2006), 12(7), 306-16; Floquet et al, *Allele-specific therapy: suppression of nonsense mutations by readthrough inducers. Med. Sci.* (Paris). (2012), 28(2), 193-199; Parenti G. *Treating lysosomal storage diseases with pharmacological chaperones: from concept to clinics. EMBO Mol Med.* (2009), 1(5), 268-279; Boyd et al., *Pharmacological chaperones as therapeutics for lysosomal storage diseases. J. Med. Chem.* (2013), 56(7), 2705-2725]. Also major progresses have been made in gene therapy, but it is still far from achieving real clinical application [Tomanin et al., *Gene therapy approaches for lysosomal storage disorders, a good model for the treatment of mendelian diseases. Acta Paediatr.* (2012), 101(7), 692-701; Haurigot et al., *Whole body correction of mucopolysaccharidosis IIIA by intracerebrospinal fluid gene therapy. J. Clin. Invest.* (2013), in press].

Pharmacological chaperone therapy has been proposed and investigated as a potential treatment for many genetic diseases that result from missense mutations leading to misfolded and/or unstable proteins without affecting the active site of the enzyme, which retain certain residual activity. Pharmacological chaperones are low-molecular-weight molecules capable of binding and stabilizing mutant proteins, thereby facilitating proper folding and transport to their site of action. Some pharmacological chaperones are able to cross the blood-brain barrier and most of them are reversible competitive inhibitors of the enzyme that bind to its catalytic site until they reach the lysosome where they might separate, narrowing the therapeutic window. This therapy is restricted to a specific type of mutation and since pharmacological chaperones are low molecular weight molecules, they can interfere in other metabolic pathways. Nowadays several pharmacological chaperones have been described for the treatment of several lysosomal diseases (Fabry, Gaucher, Gangliosidosis type I and II, Pompe, Krabbe, Batten and Sanfilippo C) [Valenzano et al, *Identification and characterization of pharmacological chaperones to correct enzyme deficiencies in lysosomal storage disorders. Assay Drug Dev. Technol.* (2011), 9(3), 213-235], but reality is that there is still no available treatment in the market.

Another possible strategy of treatment for this kind of diseases which is currently in development is the use of compounds able to induce the readthrough of premature termination codons (PTCs). This therapy is mutation-dependent and it is restricted to those cases where the protein mutation is a non-sense mutation, in other words, an amino acid mutation to a premature stop codon and mutations which create premature stop codons by reading frame shift as deletions, insertions or splicing mutations. It has been described a series of compounds, the aminoglycosides, among them gentamicin, able to induce PTCs readthrough, which allows the complete synthesis of the protein and eluding the nonsense mediated decay surveillance pathway of truncated mRNA, the Nonsense Mediated mRNA Decay (NMD). This strategy has been tested in vitro in two lysosomal storage diseases: Hurler [Keeling et al., *Gentamicin-mediated suppression of Hurler syndrome stop mutations restores a low level of alpha-L-iduronidase activity and reduces lysosomal glycosaminoglycan accumulation. Hum Mol Genet.* (2001), 10(3):291-299] and Cystinosis [Helip-Wooley et al., *Expression of CTNS alleles: subcellular localization and aminoglycoside correction in vitro. Mol. Genet. Metab.* (2002), 75(2):128-133] with promising results. Unfortunately, aminoglycosides provoke severe side-effects including oto- and nephrotoxicity, which preclude their long term use [Nudelman et al, *Repairing faulty genes by aminoglycosides: development of new derivatives of geneticin (G418) with enhanced suppression of diseases-causing nonsense mutations. Bioorg. Med. Chem.* (2010), 18(11):3735-46].

Document WO 2010/015 816 A2 proposes the treatment of lysosomal storage disorders using different iminosugars, which either inhibit the substrate synthesis avoiding its toxic accumulation, or act as pharmacological chaperones by stabilizing the defective enzyme and thereby enhancing its activity.

Document US 2013/0023488 A1 claims a high throughput screening method for identifying compounds able to reduce the intracellular accumulation of lipids. This document is based on a model of myopathy caused by an abnormal neutral lipid accumulation, for the identification of compounds able to activate the energy metabolism of fatty acids oxidation to glycolysis. While it is indicated that the methods shown could be used to find treatments in certain disorders associated to lipid and/or glycogen accumulation, no studies are provided in this regard.

Document WO 2011/109448 A1 discloses a diagnostic method for Fabry disease using androgen receptors, as well as the use of an androgen synthesis inhibitor for the treatment of Fabry disease. This document focuses exclusively on the abnormal activity of the androgen/RA metabolic pathway and on the quantification of its metabolites, not in the glycosphingolipid catabolism.

Several documents describe the use of compounds able to activate lysosomal exocytosis to treat certain lysosomal storage diseases. For example, the document [Fannie W. Chen et al. *Cyclodextrin lysosomal induce calcium-dependent exocytosis, PlosOne* (2010), 5 (11), e15054] proposes that the exocytosis mechanism is the route by which a cyclodextrin analogue decreases the accumulation of endo-lysosomal cholesterol in cells of patients suffering from Niemann-Pick type C disease. Document [Miao Xu et al. *δ-Tocopherol reduce lipid accumulation in Niemann-Pick type storage C1 and Wolman cholesterol disorders, JBC* (2012), 287 (47), 39349-39360] describes a decrease in the accumulation of cholesterol and other lipids in lysosomes, potentially by increasing lysosomal exocytosis by treatment with δ-tocopherol.

Therefore, there is a problem in the state of the art related to the lack of universal active compounds for the treatment of lysosomal storage diseases and glycogenosis, since no active compound able to act through a common mechanism to treat any kind of lysosomal storage disease has been described to date.

Bicalutamide is an oral non-steroidal anti-androgen used in the treatment of prostate cancer and hirsutism. It was first administered in 1995 in combination with chemical or surgical castration for the treatment of advanced prostate cancer and later on it was also administered as monotherapy for the treatment of earlier stages of said disease. Bicalutamide acts as a pure anti-androgen by binding to androgen receptors and by preventing their activation and the subsequent upregulation of androgen responsive genes by androgenic hormones. Bicalutamide also accelerates androgen receptors degradation. Bicalutamide is administered clinically in racemic form and the anti-androgenic activity is exclusively found in the (R)-enantiomer, being the (S)-enantiomer inactive [Mukherjee, A. et al. *Enantioselective binding of Casodex to the androgen receptor. Xenobiotica* (1996), 26 (2), 117-22]. (R)-bicalutamide is absorbed slowly and in a saturable form and is not affected by food intake. It has a half life in plasma of 1 week. (S)-bicalutamide is absorbed faster and it is eliminated from plasma. The concentrations of (R)-bicalutamide in plasma at the steady state become 100 times higher than those of (S)-bicalutamide [Cockshott Ian D. *Bicalutamide: clinical pharmacokinetics and metabolism. Clinical pharmacokinetics* (2004), 43 (13), 855-878]. Although the inactivity of (S)-bicalutamide as anti-androgen is known, it is coadministered with the (R)-enantiomer due to its low toxicity.

Surprisingly, the present invention demonstrates that the treatment of various lysosomal storage diseases with (S)-bicalutamide and/or its structural analogues, compounds without any anti-androgenic activity, is able to increase cellular exocytosis, thus decreasing the toxic accumulation of substrates inside the cells, mainly inside the lysosomes. Although the use of the androgen receptors for the treatment of a lysosomal storage disease is proposed in document WO 2011/109448 A1, there is no hint in the state of the art that the compounds described in the present invention, compounds lacking anti-androgen activity, would act increasing cellular exocytosis, and more particularly lysosomal exocytosis, since (R)-bicalutamide is the isomer with anti-androgen activity, being (S)-bicalutamide inactive as anti-androgen.

DETAILED DESCRIPTION OF THE INVENTION

The present invention solves some of the above-mentioned problems of the state of the art and provides a solution to a long-felt need of effective treatments for lysosomal storage diseases and/or disorders and/or glycogenosis. The present invention provides a treatment for lysosomal storage diseases and/or disorders and/or glycogenosis by the use of compounds that favour exocytosis, preferably lysosomal exocytosis.

The present invention describes a universal treatment of lysosomal storage diseases and/or disorders and glycogenosis by using (S)-bicalutamide and/or its structural analogues. The present invention demonstrates that the treatment of fibroblasts of patients affected by different types of lysosomal storage diseases with (S)-bicalutamide and/or its structural analogues promotes cellular exocytosis and reduces the toxic accumulation of substrates inside the cell, specially in the lysosomes. A reduction of the toxic accumulation of substrates in lysosomes allows for the treatment and/or prevention of the clinical symptoms of lysosomal storage disorders, and the present invention thus provides a solution to the existing need in the state of the art for effective treatments for this type of disorders and/or diseases.

Thus, the present invention provides a novel solution to the existing needs which comprises the use of the activity of (S)-bicalutamide and/or its structural analogues for the treatment of lysosomal storage diseases and/or disorders and/or glycogenosis by the effective activation of cellular exocytosis. The universality of the treatment with (S)-bicalutamide and/or its structural analogues is here demonstrated by the promising results obtained in the different disorders tested, differing from known treatments in the state of the art, which are specific for each disorder. The invention also demonstrates the importance of the stereochemistry of the chiral center of bicalutamide and/or its structural analogues, standing out the efficacy of the (S)-enantiomer in comparison with the (R)-enantiomer. Surprisingly, (S)-bicalutamide favours exocytosis in a more effective way than its enantiomer (R)-bicalutamide. Thus, (R)-bicalutamide is ineffective in most of the diseases tested and shows a scarce efficacy in others (although this enantiomer shows efficacy in some of the tested diseases, its activity is not statistically significant), whereas (S)-bicalutamide is effective in all the diseases tested. The invention also demonstrates that (S)-bicalutamide and/or its structural analogues (compounds lacking anti-androgen activity) can be used for the treatment and/or prevention of the damaging clinical symptoms of lysosomal storage diseases and/or disorders and/or glycogenosis. This represents an advantage for the treatment of LSDs in children, since the treatment with bicalutamide (racemic mixture) delays their sexual development, due to the anti-androgenic action of the (R)-bicalutamide enantiomer. Furthermore, the lack of anti-androgen activity of (S)-bicalutamide would prevent the damaging side effects found in chronic treatments of prostate cancer with the racemic mixture, derived from the anti-androgen activity of the (R)-bicalutamide enantiomer.

Definitions

Herein included are the meaning of some terms and expressions as they are employed in the context of the invention, with the aim of aiding the comprehension of the present invention.

In the context of the invention, the term "bicalutamide" refers to all forms of bicalutamide, such as its racemic mixture or their individual enantiomers (S)-bicalutamide (1) and (R)-bicalutamide (2), or a pharmaceutically acceptable salt, hydrate or solvate thereof. Structures of (S)-bicalutamide [(2S)-N-[4-cyano-3-(trifluoromethyl)phenyl]-3-[(4-fluorophenyl)sulfonyl]-2-hydroxy-2-methylpropanamide] (1) and (R)-bicalutamide [(2R)-N-[4-cyano-3-(trifluoromethyl)phenyl]-3-[(4-fluorophenyl)sulfonyl]-2-hydroxy-2-methylpropanamide] (2) are described below:

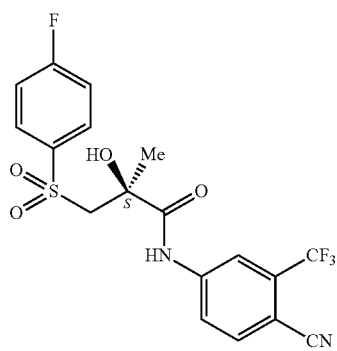

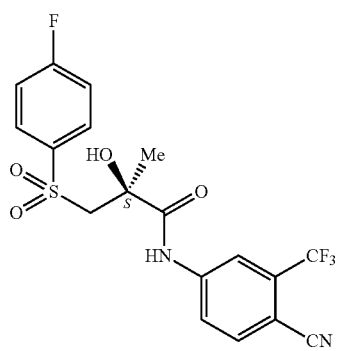

(S)-Bicalutamide (1) and (R)-bicalutamide (2) structures

The term "individual" refers to any organism to which compounds described in the present invention can be administered, being the administration for experimental, diagnostic and/or therapeutic purposes. The individual can be a cell, an animal or a human.

The term "treatment", as used herein, means the administration of a compound according to the invention in order to ameliorate the adverse clinical symptoms caused by a disease and/or disorder, or to reduce or eliminate the incidence or severity of one or more symptoms or physiological effects associated to said disease or disorder. The treatment is administered before, during, and/or after the initial symptoms. The treatment can be administered to an individual who doesn't show any symptom of disease and/or disorder, to an individual who presents the initial symptoms of the disease and/or disorder, or to an individual who presents an abundance of symptoms in an advanced stage of the disease and/or disorder.

In the context of the invention, the term "diagnosis" refers to diagnostic methods performed in the absence of the human body.

The term "prevention", as used herein, refers to the ability of a compound of the invention to delay or difficult the development of a disease and/or disorder, as well as its ability to delay the appearance of symptoms or to improve them.

In the context of the invention, the term "therapeutic dose" refers to the necessary amount of a compound disclosed in the invention that must be administered to an individual in order to obtain a medical or biological positive response, being the individual a cell, an animal or a human being, and being the compound administered by a researcher, a physician, a veterinary or by the individual himself or herself.

In the context of the invention, the term "therapeutic agent" refers to any agent or compound that produces a desirable pharmacological effect in an individual.

The term "combination therapy", as used herein, refers to those situations where two or more different therapeutic agents are administered together to an individual, being the individual exposed to both therapeutic agents. For example, a compound of the invention can be jointly administered with another therapeutic agent either simultaneously or sequentially, in separated unitary doses or in the same unitary dose. The term "sequential" means that a therapeutic agent of the invention can be administered before, during, or after the administration of another therapeutic agent. The terms "combination therapy" and the use of compounds "in combination" are equivalent terms and they are used in the present invention to refer to compounds or agents which are administered as part of the same treatment.

In the context of the invention, the terms "activity" or "pharmacological activity" refer to the biological or medical response as a result of the treatment of an individual with a compound disclosed in the present invention, being the individual a cell, an animal, or a human being, and being the compound administered by a researcher, a physician, a veterinary or by the individual himself or herself. In a particular embodiment of this invention, the term "enzymatic activity" refers to the biological or medical response of an enzyme as a result of the treatment of an individual with a compound disclosed in the invention. The activity expresses the amount of converted substrate per time unit, taking into account the reaction volume.

In the context of the invention, the chemical term "enantiomer" refers to one of the two stereoisomers of a molecule, each of which is the specular image of the other, and therefore they are not superposable (they are not identical). The two possible enantiomers of a molecule having one chiral center are defined as (R) or (S) enantiomers and their definition can be found in the IUPAC rules [International Union of Pure and Applied Chemistry, *Basic terminology of stereochemistry*, PAC (1996), 68(12), 2193-2222]. The person skilled in the art can unequivocally identify the enantiomers of a chiral molecule.

In the context of the invention, the chemical term "structural analogue" refers to a compound that has a similar structure to another compound, but differs in certain components. The components in which both analogues differ can be atoms, functional groups or substructures, which are replaced by other atoms, by other functional groups, or by other substructures.

In the context of the invention, the chemical term "functional analogue" refers to a structural analogue that shares the same kind of pharmacological activity than the compound with which it is compared.

In the context of the invention, the chemical term "structure" refers to the group of atoms and bonds that form a molecule.

In the context of the invention, the chemical term "substructure" refers to a specific part of a structure, said structure being formed by a concrete and perfectly defined group of substructures.

In the context of the invention, the chemical term "functional group" refers to a group of atoms or bonds inside the molecule which have a characteristic chemical reactivity and further provides the molecule with characteristic functional properties. The same functional group has similar chemical reactivity properties independently of the size of the molecule that contains it.

The term "non-cyclic aliphatic group" is used in this invention to cover the linear or branched alkyl, alkenyl and alkynyl groups.

The term "alkyl group" refers to a saturated, linear or branched group, which has between 1 and 24, preferably between 1 and 16, more preferably between 1 and 14, even more preferably between 1 and 12, yet more preferably 1, 2, 3, 4, 5, or 6 carbon atoms and that is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and such like.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more carbon-carbon double bonds, preferably with 1, 2 or 3 carbon-carbon double bonds, conjugated or unconjugated, which is bound to the rest of the molecule by a single bond, including, for example and not restricted to, the vinyl ($-CH_2=CH_2$), allyl ($-CH_2-CH=CH_2$), oleyl, linoleyl groups and such like.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more carbon-carbon triple bonds, preferably 1, 2 or 3 carbon-carbon triple bonds, conjugated or unconjugated, which is bound to the rest of the molecule by a single bond, including, for example and not restricted to, the ethynyl group, 1-propinyl, 2-propinyl, 1-butinyl, 2-butinyl, 3-butinyl, pentinyl, such as 1-pentinyl and such like. The alkynyl groups can also contain one or more carbon-carbon double bonds, including, for example and not restricted to, the but-1-en-3-inyl, pent-4-en-1-inyl groups and such like.

The term "halogen" refers to an atom of fluorine (F), chlorine (Cl), bromine (Br) or iodine (I).

The term "haloalkane group" refers to a saturated, linear or branched group, which has between 1 and 24, preferably between 1 and 16, more preferably between 1 and 14, even more preferably between 1 and 12, yet more preferably 1, 2, 3, 4, 5 or 6 carbon atoms, derived from an alkane group by substitution of one or more hydrogen atoms by halogen atoms, which is bound to the rest of the molecule by a simple bond, including, for example and not restricted to, trifluoromethyl, trichloromethyl, trifluorobutyl, tribromopropyl, dibromomethyl and such like. The term "perfluoroalkyl group" refers to a group where all hydrogen atoms have been replaced by halogen atoms.

The term "alicyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and such like.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more carbon-carbon double bonds, preferably 1, 2 or 3 carbon-carbon double bonds, conjugated or unconjugated, which is bound to the rest of the molecule by a single bond, including, for example and not restricted to, the cyclopent-1-en-1-yl group and such like.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 carbon-carbon triple bonds, conjugated or unconjugated, which is bound to the rest of the molecule by a single bond, including, for example and not restricted to, the cyclooct-2-in-1-yl group and such like. Cycloalkynyl groups can also contain one or more carbon-carbon double bonds, including, for example and not restricted to, the cyclooct-4-en-2-inyl group and such like.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl, among others; or to an aralkyl group.

The term "aralkyl group" refers to an alkyl group substituted by an aromatic group, with between 7 and 24 carbon atoms and including, for example and not restricted to, $-(CH_2)_{1-6}$-phenyl, $-(CH_2)_{1-6}$-(1-naphthyl), $-(CH_2)_{1-6}$-(2-naphthyl), $-(CH_2)_{1-6}-CH(phenyl)_2$ and such like.

The term "heterocyclyl group" refers to a hydrocarbonated ring of 3-10 members, in which one or more of the atoms of the ring, preferably 1, 2 or 3 of the atoms of the ring, is an element other than carbon, such as for example nitrogen, oxygen or sulfur and which may be saturated or unsaturated. For the purposes of this invention, the heterocycle can be a cyclic, monocyclic, bicyclic or tricyclic system, which may include fused ring systems; and the nitrogen, carbon or sulfur atoms may optionally be oxidized in the heterocyclyl radical; the nitrogen atom may optionally be quaternized; and the heterocyclyl radical may be partially or completely saturated or may be aromatic. More preferably, the term heterocyclyl refers to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups, are pyridine, pyrrol, furan, thiophene, benzofuran, imidazoline, quinolein, quinoline, pyridazine and naphthyridine.

The term "heteroarylalkyl group" refers to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, $-(CH_2)_{1-6}$-imidazolyl, $-(CH_2)_{1-6}$-triazolyl, $-(CH_2)_{1-6}$-thienyl, $-(CH_2)_{1-6}$-furyl, $-(CH_2)_{1-6}$-pyrrolidinyl and such like.

As is understood in this technical field, there may be a certain degree of substitution in the groups defined above. Therefore, there may be substitution in the groups of this invention where this is explicitly indicated. The references in this document to substituted groups in the groups of this invention indicate that the specified radical can be substituted in one or more available positions with one or more substituents, preferably in 1, 2 or 3 positions, more preferably in 1 or 2 positions, yet more preferably in 1 position.

Compounds for Use in the Invention

Thus, in a first aspect, the present invention relates to the compound (S)-bicalutamide and/or a structural analogue collectively defined by the general formula (I)

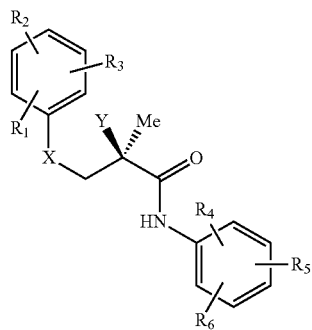

(I)

their pharmaceutically acceptable salts, their hydrates and/or their solvates, wherein:

$R_1$, $R_2$ and $R_3$ are independently selected from the group consisting of H, substituted or unsubstituted non-cyclic aliphatic group, substituted or unsubstituted alicyclyl group, substituted or unsubstituted heterocyclyl group, substituted or unsubstituted heteroarylalkyl group, substituted or unsubstituted aryl group, substituted or unsubstituted aralkyl group, amino, aminoalkyl, alkylamido, substituted or unsubstituted acylamido, alkoxyl, substituted or unsubstituted alkylsulfonyl, alkylthio, aminoacyl, alkanoylamino, aminodiacyl, dialkanoylamino, aryloxyl, azido, carbonyloxyl, nitrile, substituted or unsubstituted diacylamido, halogen, isothiocyanate, substituted or unsubstituted non-cyclic haloalkane, substituted or unsubstituted cyclic haloalkane, perfluoroalkane, hydroxyl, isothiocyanate, nitro, oxycarbonyl, thiol, substituted or unsubstituted thioether;

$R_4$, $R_5$ and $R_6$ are independently selected from the group consisting of H, substituted or unsubstituted non-cyclic aliphatic group, substituted or unsubstituted alicyclyl group, substituted or unsubstituted heterocyclyl group, substituted or unsubstituted heteroarylalkyl group, substituted or unsubstituted aryl group, substituted or unsubstituted aralkyl group, amino, aminoalkyl, alkylamido, substituted or unsubstituted acylamido, alkoxyl, substituted or unsubstituted alkylsulfonyl, alkylthio, aminoacyl, aryloxyl, azido, carbonyloxyl, nitrile, substituted or unsubstituted diacylamido, halogen, isothiocyanate, substituted or unsubstituted non-cyclic haloalkane, substituted or unsubstituted cyclic haloalkane, perfluoroalkane, hydroxyl, isothiocyanate, nitro, oxycarbonyl, thiol, substituted or unsubstituted thioether;

X is selected from the group consisting of S, SO, $SO_2$ or O;

Y is selected from the group consisting of hydrogen, —OH, —OR or —CONHR, wherein R is an alkyl, haloalkyl, dihaloalkyl, trihaloalkyl, aryl, phenyl, halogen, alkenyl or glycosyl group or a polyethylene glycol polymer;

for use in the diagnosis, prevention of clinical symptoms, and/or treatment of lysosomal storage diseases and/or disorders and/or glycogenosis.

Preferably, $R_1$, $R_2$ and $R_3$ are independently selected from the group consisting of H, alkyl, halogen, haloalkane, amino, aminoalkyl, aminoacyl, alkanoylamino, acylamido, alkylamido, aminodiacyl, diacylamido, dialkanoylamino, azido, carbonyloxyl, nitrile, nitro and hydroxyl. More preferably, $R_1$, $R_2$ and $R_3$ are independently selected from the group consisting of H, halogen, amino, aminoacyl, alkanoylamino, diacylamido, dialkanoylamino, nitrile, isothiocyanate and hydroxyl. Even more preferably, $R_1$, $R_2$ and $R_3$ are independently selected from the group consisting of H, halogen, amino, acetamido, alkylamido, haloalkylamido, alkanoylamino, dialkanolylamino, nitrile and isothiocyanate.

Preferably, $R_4$, $R_5$ and $R_6$ are independently selected from the group consisting of H, alkyl, halogen, haloalkane, perfluoroalkane, nitrile, isothiocyanate, nitro, azido, aminoacyl, acylamido, carbonyloxyl and hydroxyl. More preferably, $R_4$, $R_5$ and $R_6$ are independently selected from the group consisting of H, halogen, haloalkane, perfluoroalkane, nitrile, isothiocyanate, nitro and hydroxyl. Even more preferably, $R_4$, $R_5$ and $R_6$ are independently selected from the group consisting of H, halogen, trifluoromethyl, nitrile, isothiocyanate and nitro.

Preferably, Y is selected from the group consisting of —OH, —OR or —CONHR, wherein R is an alkyl, haloalkyl or glycosyl group or a polyethylene glycol polymer.

According to a preferred embodiment, in the compound of general formula (I), $R_1$ is selected from the group consisting of hydrogen (H), halogen (F, Cl, Br or I), amino (—$NH_2$), acetamido (—$NHCOCH_3$), propionamido (—NHCOEt), N,N-diacetamido (—$NAc_2$), N,N-dipropionamido (—$N(COEt)_2$), 2-chloroacetamido (—$NHCOCH_2Cl$), nitrile (—CN) or isothiocyanate (—NCS) group; $R_2$ and $R_3$ are hydrogen (H); $R_4$ is a trifluoromethyl group (—CF) or hydrogen (H); $R_5$ is a nitrile (—CN) or a nitro (—$NO_2$) group; $R_6$ is hydrogen (H), X is thioether (S), sulfoxide (SO), sulfone ($SO_2$) or oxygen (O), and Y is a hydroxyl group (OH). Preferably, $R_4$ is in the meta position and $R_5$ is in the para position, and the compounds are defined by the general formula (II):

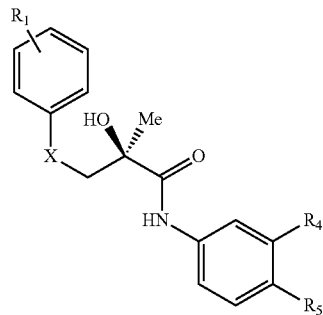

(II)

Thus, in a preferred embodiment, the present invention relates to the compound (S)-bicalutamide and/or a structural analogue collectively defined by the general formula (II)

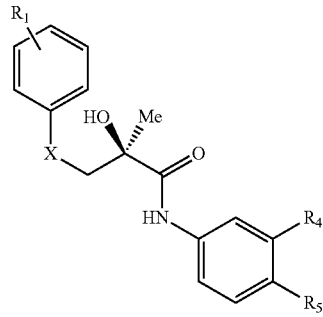

(II)

their pharmaceutically acceptable salts, their hydrates and/or their solvates, wherein:

R₁ is hydrogen (H), halogen (F, Cl, Br or I), amino (—NH₂), acetamido (—NHCOCH₃), propionamido (—NHCOEt), N,N-diacetamido (—NAc₂), N,N-dipropionamido (—N(COEt)₂), 2-chloroacetamido (—NHCOCH₂Cl), nitrile (—CN) or isothiocyanate (—NCS) group;

R₄ is a trifluoromethyl group (—CF₃) or hydrogen (H);

R₅ is a nitrile (—CN) or a nitro (—NO₂) group;

X is thioether (S), sulfoxide (SO), sulfone (SO₂) or oxygen (O);

for use in the diagnosis, prevention of clinical symptoms, and/or treatment of lysosomal storage diseases and/or disorders, and/or glycogenosis.

In a more preferred embodiment, in the compound of general formula (I), R₁ is fluorine (F) in the para-position, R₂ and R₃ are hydrogen (H), R₄ is a trifluoromethyl group (CF₃) in the meta position, R₅ is a nitrile group (CN) in the para position, R₆ is hydrogen (H), X is thioether (S), sulfoxide (SO) or sulfone (SO₂), and Y is a hydroxyl group (OH). In an equivalent manner, in the compound of general formula (II), R₁ is fluorine (F) in the para position, R₄ is a trifluoromethyl group (CF₃), R₅ is a nitrile group (CN) and X is thioether (S), sulfoxide (SO) or sulfone (SO₂).

According to an even more preferred embodiment, in the compound of general formula (I), R₁ is fluorine (F) in the para position, R₂ and R₃ are hydrogen (H), R₄ is a trifluoromethyl group (CF₃) in the meta position, R₅ is a nitrile group (CN) in the para position, R₆ is hydrogen (H), X is sulfone (SO₂) and Y is a hydroxyl group (OH), corresponding to the (S)-bicalutamide structure [(2S)—N-[4-cyano-3-(trifluoromethyl)phenyl]-3-[(4-fluorophenyl)sulfonyl]-2-hydroxy-2-methylpropanamide] (1). In an equivalent manner, in the compound of general formula (II), R₁ is fluorine (F) in the para position, R₄ is a trifluoromethyl group (CF₃), R₅ is a nitrile group (CN) and X is sulfone (SO₂), corresponding to (S)-bicalutamide (1). Thus, in a preferred embodiment, the present invention relates to (S)-bicalutamide for use in the diagnosis, prevention of clinical symptoms, and/or treatment of lysosomal storage diseases and/or disorders, and/or glycogenosis.

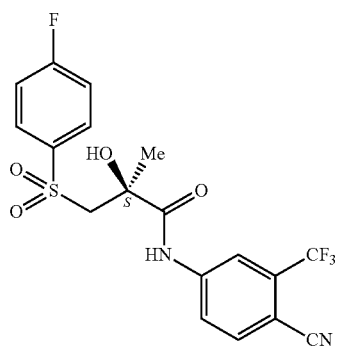

(1)

According to an even more preferred embodiment, in the compound of general formula (I), R₁ is fluorine (F) in the para position, R₂ and R₃ are hydrogen (H), R₄ is a trifluoromethyl group (CF₃) in the meta position, R₅ is a nitrile group (CN) in the para position, R₆ is hydrogen (H), X is sulfoxide (SO) and Y is a hydroxyl group (OH) (3). In an equivalent manner, in the compound of general formula (II), R₁ is fluorine (F) in the para position, R₄ is a trifluoromethyl group (CF₃) in the meta position, R₅ is a nitrile group (CN) in the para position, and X is sulfoxide (SO) (3).

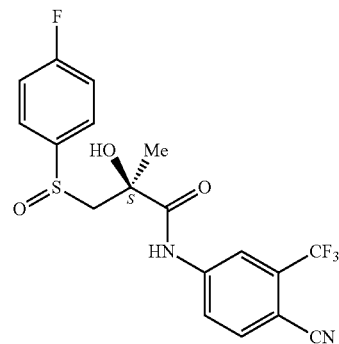

(3)

According to an even more preferred embodiment, in the compound of general formula (I), R₁ is fluorine (F) in the para position, R₂ and R₃ are hydrogen (H), R₄ is a trifluoromethyl group (CF₃) in the meta position, R₅ is a nitrile group (CN) in the para position, R₆ is hydrogen (H), X is thioether (S) and Y is a hydroxyl group (OH) (4). In an equivalent manner, in the compound of general formula (II), R₁ is fluorine (F) in the para position, R₄ is a trifluoromethyl group (CF₃) in the meta position, R₅ is a nitrile group (CN) in the para position, and X is thioether (S) (4).

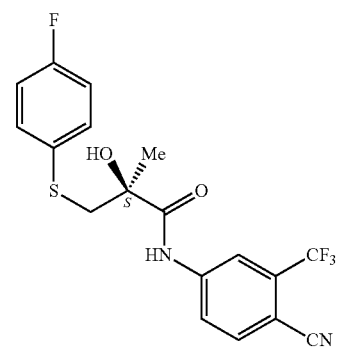

(4)

According to another preferred embodiment, in the compound of general formula (I), R₁ is iodine (I) in the para position, R₂ and R₃ are hydrogen (H), R₄ is a trifluoromethyl group (CF₃) in the meta position, R₅ is a nitrile group (CN) in the para position, R₆ is hydrogen (H), X is sulfone (SO₂), and Y is a hydroxyl group (OH) (5). In an equivalent manner, in the compound of general formula (II), R₁ is iodine (I) in the para position, R₄ is a trifluoromethyl group (CF₃) in the meta position, R₅ is a nitrile group (CN) in the para position, and X is sulfone (SO₂) (5).

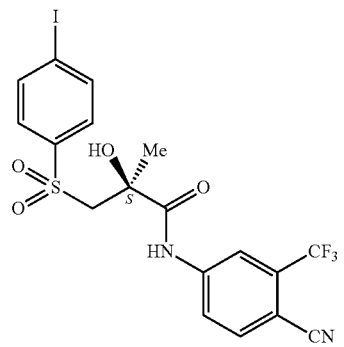

(5)

According to another preferred embodiment, in the compound of general formula (I), $R_1$ is an acetamido group (NHAc) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is sulfone ($SO_2$), and Y is a hydroxyl group (OH) (6). In an equivalent manner, in the compound of general formula (II), $R_1$ is an acetamido group (NHAc) in the para position, $R_4$ is a trifluoromethyl group ($CF_3$) in the meta position, $R_5$ is a nitrile group (CN) in the para position, and X is sulfone ($SO_2$) (6).

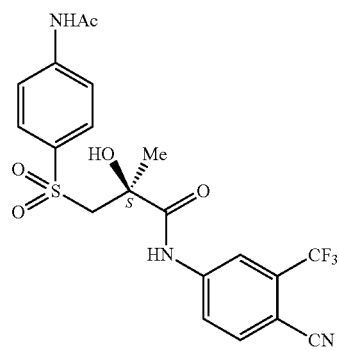

(6)

According to another preferred embodiment, in the compound of general formula (I), $R_1$ is a 2-chloroacetamido group in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is sulfone ($SO_2$), and Y is a hydroxyl group (OH) (7). In an equivalent manner, in the compound of general formula (II), $R_1$ is a 2-chloroacetamido group in the para position, $R_4$ is a trifluoromethyl group ($CF_3$) in the meta position, $R_5$ is a nitrile group (CN) in the para position, and X is sulfone ($SO_2$) (7).

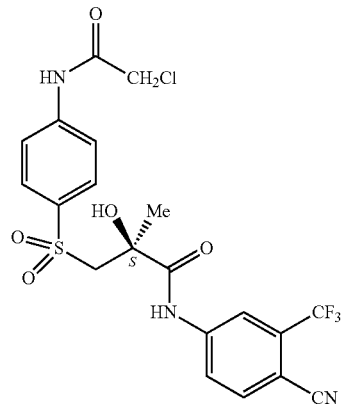

(7)

According to another preferred embodiment, in the compound of general formula (I), $R_1$ is an acetamido group (NHAc) in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is sulfone ($SO_2$), and Y is a hydroxyl group (OH) (8). In an equivalent manner, in the compound of general formula (II), $R_1$ is an acetamido group (NHAc) in the para position, $R_4$ is a trifluoromethyl group ($CF_3$) in the meta position, $R_5$ is a nitro group ($NO_2$) in the para position, and X is sulfone ($SO_2$) (8).

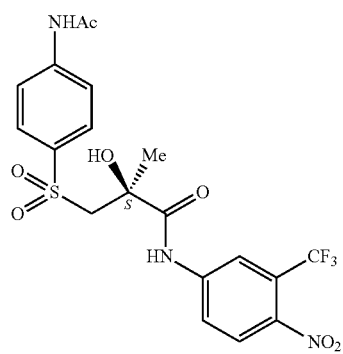

(8)

According to another preferred embodiment, in the compound of general formula (I), $R_1$ is a 2-chloroacetamido group in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is sulfone ($SO_2$), and Y is a hydroxyl group (OH) (9). In an equivalent manner, in the compound of general formula (II), $R_1$ is a 2-chloroacetamido group in the para position, $R_4$ is a trifluoromethyl group ($CF_3$) in the meta position, $R_5$ is a nitro group ($NO_2$) in the para position, and X is sulfone ($SO_2$) (9).

(9)

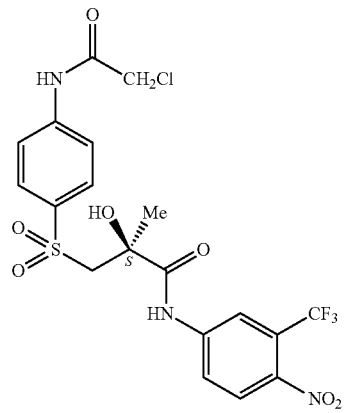

According to another preferred embodiment, in the compound of general formula (I), $R_1$ is iodine in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (10). In an equivalent manner, in the compound of general formula (II), $R_1$ is iodine (I) in the para position, $R_4$ is a trifluoromethyl group ($CF_3$) in the meta position, $R_5$ is a nitrile group (CN) in the para position, and X is thioether (S) (10).

(10)

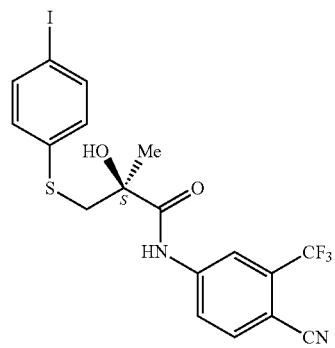

According to another preferred embodiment, in the compound of general formula (I), $R_1$ is an isothiocyanate group (—NCS) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (11). In an equivalent manner, in the compound of general formula (II), $R_1$ is an isothiocyanate group (—NCS) in the para position, $R_4$ is a trifluoromethyl group ($CF_3$) in the meta position, $R_5$ is a nitrile group (CN) in the para position, and X is thioether (S) (11).

(11)

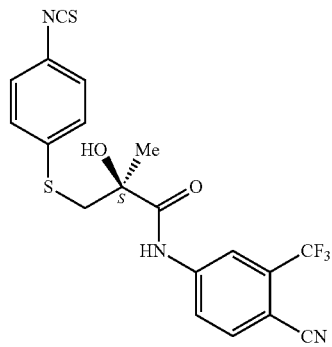

According to another preferred embodiment, in the compound of general formula (I), $R_1$ is an isothiocyanate group (—NCS) in the meta position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (12). In an equivalent manner, in the compound of general formula (II), $R_1$ is an isothiocyanate group (—NCS) in the meta position, $R_4$ is a trifluoromethyl group ($CF_3$) in the meta position, $R_5$ is a nitrile group (CN) in the para position, and X is thioether (S) (12).

(12)

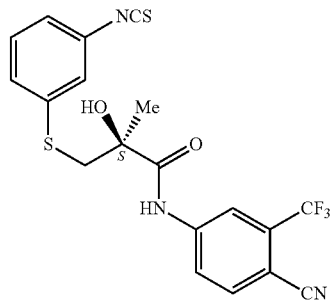

According to another preferred embodiment, in the compound of general formula (I), $R_1$ is an amino group ($NH_2$) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (13). In an equivalent manner, in the compound of general formula (II), $R_1$ is an amino group ($NH_2$) in the para position, $R_4$ is a trifluoromethyl group ($CF_3$) in the meta position, $R_5$ is a nitrile group (CN) in the para position, and X is thioether (S) (13).

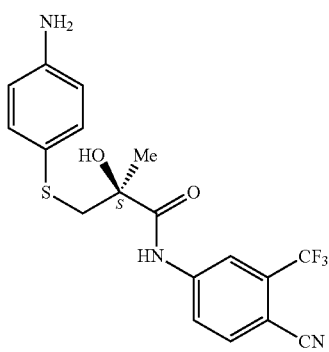

(13)

According to another preferred embodiment, in the compound of general formula (I), $R_1$ is an amino group ($NH_2$) in the meta position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (14). In an equivalent manner, in the compound of general formula (II), $R_1$ is an amino group ($NH_2$) in the meta position, $R_4$ is a trifluoromethyl group ($CF_3$) in the meta position, $R_5$ is a nitrile group (CN) in the para position, and X is thioether (S) (14).

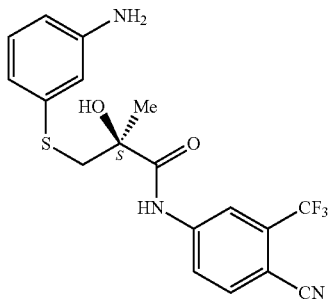

(14)

According to another preferred embodiment, in the compound of general formula (I), $R_1$ is an acetamido group (NHAc) in para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (15). In an equivalent manner, in the compound of general formula (II), $R_1$ is an acetamido group (NHAc) in the para position, $R_4$ is a trifluoromethyl group ($CF_3$) in the meta position, $R_5$ is a nitrile group (CN) in the para position, and X is thioether (S) (15).

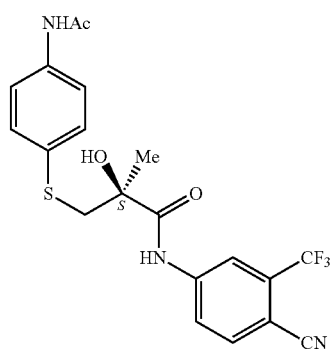

(15)

According to another preferred embodiment, in the compound of general formula (I), $R_1$ is a 2-chloroacetamido group in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (16). In an equivalent manner, in the compound of general formula (II), $R_1$ is 2-chloroacetamido group in the para position, $R_4$ is a trifluoromethyl group ($CF_3$) in the meta position, $R_5$ is a nitrile group (CN) in the para position, and X is thioether (S) (16).

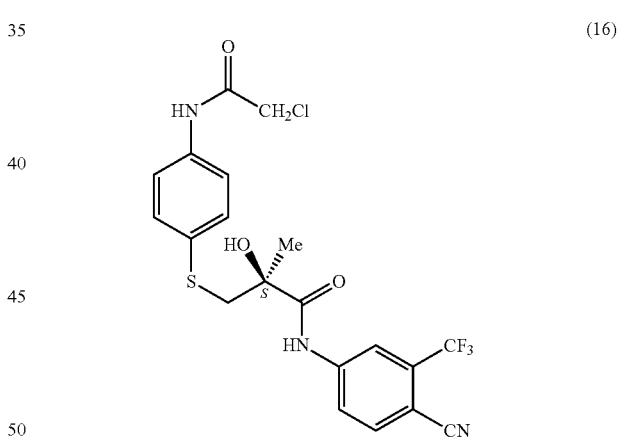

(16)

According to another preferred embodiment, in the compound of general formula (I), $R_1$ is a N,N-diacetamido group ($NAc_2$) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (17). In an equivalent manner, in the compound of general formula (II), $R_1$ is a N,N-diacetamido group ($NAc_2$) in the para position, $R_4$ is a trifluoromethyl group ($CF_3$) in the meta position, $R_5$ is a nitrile group (CN) in the para position, and X is thioether (S) (17).

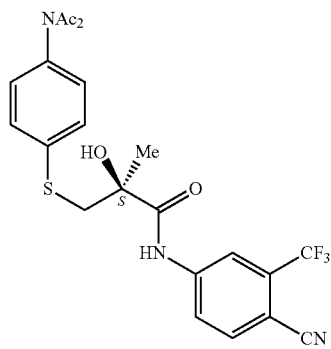

(17)

According to another preferred embodiment, in the compound of general formula (I), $R_1$ is a propionamido group in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (18). In an equivalent manner, in the compound of general formula (II), $R_1$ is a propionamido group in the para position, $R_4$ is a trifluoromethyl group ($CF_3$) in the meta position, $R_5$ is a nitrile group (CN) in the para position, and X is thioether (S) (18).

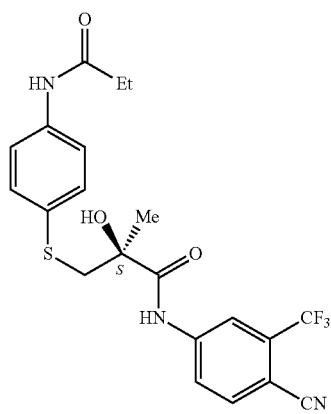

(18)

According to another preferred embodiment, in the compound of general formula (I), $R_1$ is a N,N-dipropionamido group in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is thioether (S), and Y is a hydroxyl group (OH) (19). In an equivalent manner, in the compound of general formula (II), $R_1$ is a N,N-dipropionamido group in the para position, $R_4$ is a trifluoromethyl group ($CF_3$) in the meta position, $R_5$ is a nitrile group (CN) in the para position, and X is thioether (S) (19).

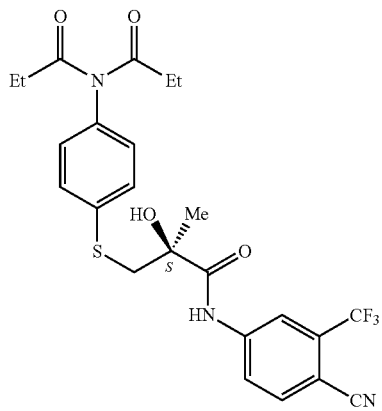

(19)

According to another preferred embodiment, in the compound of general formula (I), $R_1$ is an amino group ($NH_2$) in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is thioether (S), and Y is a hydroxyl group (OH) (20). In an equivalent manner, in the compound of general formula (II), $R_1$ is an amino group ($NH_2$) in the para position, $R_4$ is a trifluoromethyl group ($CF_3$) in the meta position, $R_5$ is a nitro group ($NO_2$) in the para position, and X is thioether (S) (20).

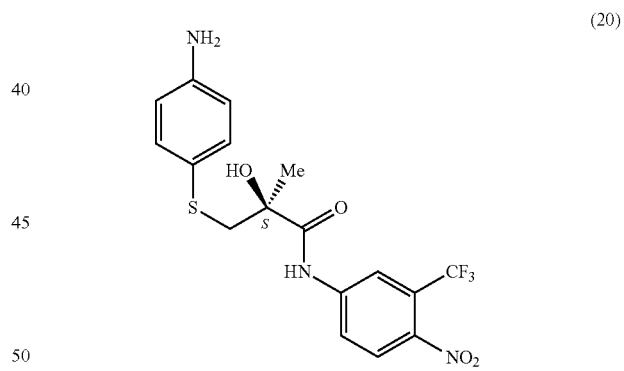

(20)

According to another preferred embodiment, in the compound of general formula (I), $R_1$ is an acetamido group (NHAc) in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is thioether (S), and Y is a hydroxyl group (OH) (21). In an equivalent manner, in the compound of general formula (II), $R_1$ is an acetamido group (NHAc) in the para position, $R_4$ is a trifluoromethyl group ($CF_3$) in the meta position, $R_5$ is a nitro group ($NO_2$) in the para position, and X is thioether (S) (21).

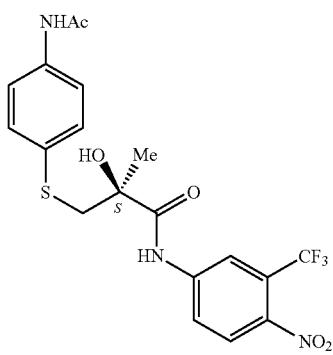

(21)

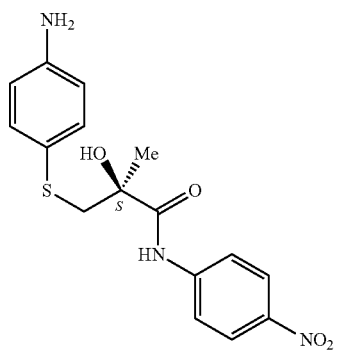

(23)

According to another preferred embodiment, in the compound of general formula (I), $R_1$ is an 2-chloroacetamido group in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is thioether (S), and Y is a hydroxyl group (OH) (22). In an equivalent manner, in the compound of general formula (II), $R_1$ is a 2-chloroacetamido group in the para position, $R_4$ is a trifluoromethyl group ($CF_3$) in the meta position, $R_5$ is a nitro group ($NO_2$) in the para position, and X is thioether (S) (22).

According to another preferred embodiment, in the compound of general formula (I), $R_1$ is a 2-chloroacetamido group in the para position, $R_2$ and $R_3$ are hydrogen (H), $R_4$ is a nitro group ($NO_2$) in the para position, $R_5$ and $R_6$ are hydrogen (H), X is thioether (S), and Y is a hydroxyl group (OH) (24). In an equivalent manner, in the compound of general formula (II), $R_1$ is a 2-chloroacetamido group in the para position, $R_4$ is hydrogen (H), $R_5$ is a nitro group ($NO_2$) in the para position, and X is thioether (S) (24).

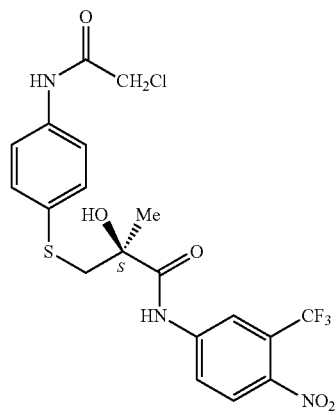

(22)

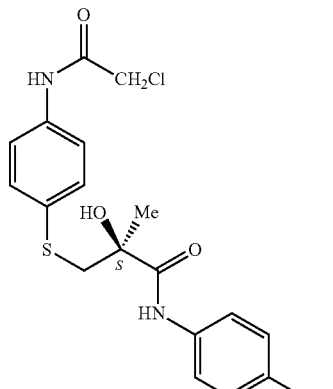

(24)

According to another preferred embodiment, in the compound of general formula (I), $R_1$ is an amino group ($NH_2$) in the para position, $R_2$ and $R_3$ are hydrogen (H), $R_4$ is a nitro group ($NO_2$) in the para position, $R_5$ and $R_6$ are hydrogen (H), X is a thioether (S), and Y is a hydroxyl group (OH) (23). In an equivalent manner, in the compound of general formula (II), $R_1$ is an amino group ($NH_2$) in the para position, $R_4$ is hydrogen (H), $R_5$ is a nitro group ($NO_2$) in the para position, and X is thioether (S) (23).

According to another preferred embodiment, in the compound of general formula (I), $R_1$ is an isothiocyanate group (SCN—) in the para position, $R_2$ and $R_3$ are hydrogen (H), $R_4$ is a nitro group ($NO_2$) in the para position, $R_5$ and $R_6$ are hydrogen (H), X is thioether (S), and Y is a hydroxyl group (OH) (25). In an equivalent manner, in the compound of general formula (II), $R_1$ is an isothiocyanate group (SCN—) in the para position, $R_4$ is hydrogen (H), $R_5$ is a nitro group ($NO_2$) in the para position, and X is thioether (S) (25).

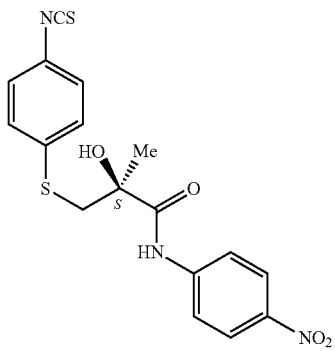

(25)

According to another preferred embodiment, in the compound of general formula (I), $R_1$, $R_2$ and $R_3$ are hydrogen (H), $R_4$ is a nitrile group (CN) in the meta position, $R_5$ is a trifluoromethyl group ($CF_3$) in the para position, $R_6$ is hydrogen (H), X is thioether (S), and Y is a hydroxyl group (OH) (26). In an equivalent manner, in the compound of general formula (II), $R_1$ is hydrogen (H) in the para position, $R_4$ is a nitrile group (CN) in the meta position, $R_5$ is a trifluoromethyl group ($CF_3$) in the para position, and X is thioether (S) (26).

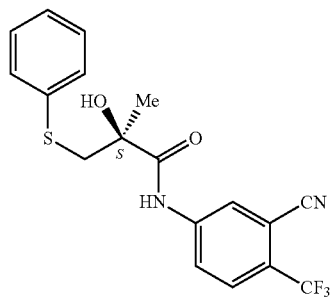

(26)

According to another preferred embodiment, in the compound of general formula (I), $R_1$ is a nitrile group (CN) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is oxygen (O), and Y is a hydroxyl group (OH) (27). In an equivalent manner, in the compound of general formula (II), $R_1$ is nitrile group (CN) in the para position, $R_4$ is a trifluoromethyl group ($CF_3$) in the meta position, $R_5$ is a nitrile group (CN) in the para position, and X is oxygen (O) (27).

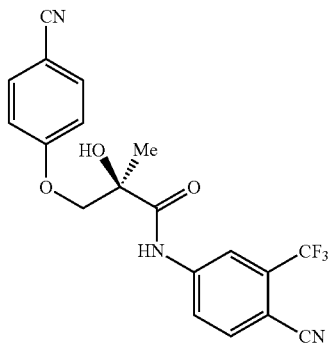

(27)

According to another preferred embodiment, in the compound of general formula (I), $R_1$ is an acetamido group (NHAc) in the para position, $R_2$ and $R_3$ are hydrogen (H), $R_4$ is a trifluoromethyl group ($CF_3$) in the meta position, $R_5$ is a nitro group ($NO_2$) in the para position, $R_6$ is hydrogen (H), X is oxygen (O), and Y is a hydroxyl group (OH) (28). In an equivalent manner, in the compound of general formula (II), $R_1$ is an acetamido group (NHAc) in the para position, $R_4$ is a trifluoromethyl group ($CF_3$) in the meta position, $R_5$ is a nitro group ($NO_2$) in the para position, and X is oxygen (O) (28).

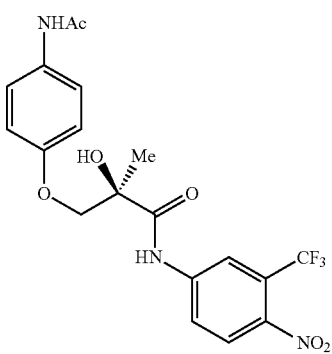

(28)

According to another preferred embodiment, in the compound of general formula (I), $R_1$ is chlorine (Cl) in the para position, $R_2$ and $R_3$ are hydrogen (H), $R_4$ is a methyl group ($CH_3$) in the meta position, $R_5$ is a nitrile group (CN) in the para position, $R_6$ is hydrogen (H), X is oxygen (O), and Y is a hydroxyl group (OH) (29). In an equivalent manner, in the compound of general formula (II), $R_1$ is chlorine (Cl) in the para position, $R_4$ is a methyl group ($CH_3$) in the meta position, $R_5$ is a nitrile group (CN) in the para position, and X is oxygen (O) (29).

(29)

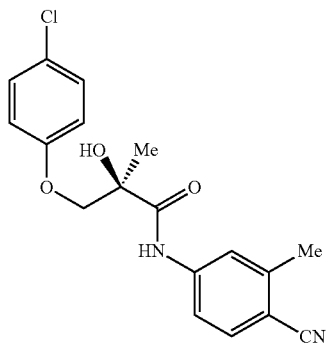

According to another preferred embodiment, in the compound of general formula (I), $R_1$ is fluorine (F) in the para position, $R_2$ and $R_3$ are hydrogen (H), $R_4$ is a trifluoromethyl group ($CF_3$) in the meta position, $R_5$ is a nitrile group (CN) in the para position, $R_6$ is hydrogen (H), X is oxygen (O), and Y is a hydroxyl group (OH) (30). In an equivalent manner, in the compound of general formula (II), $R_1$ is fluorine (F) in the para position, $R_4$ is a trifluoromethyl group ($CF_3$) in the meta position, $R_5$ is a nitrile group (CN) in the para position, and X is oxygen (O) (30).

(30)

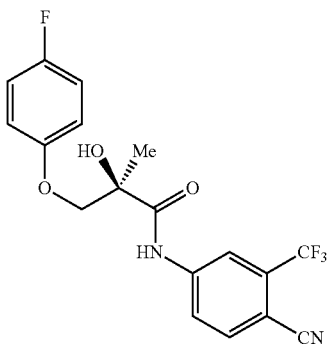

According to another preferred embodiment, in the compound of general formula (I), $R_1$ is fluorine (F) in the meta position, $R_2$ is chlorine (Cl) in the para position, $R_3$ is hydrogen (H), $R_4$ is a trifluoromethyl group ($CF_3$) in the meta position, $R_5$ is a nitro group ($NO_2$) in the para position, $R_6$ is hydrogen (H), X is oxygen (O), and Y is a hydroxyl group (OH) (31).

(31)

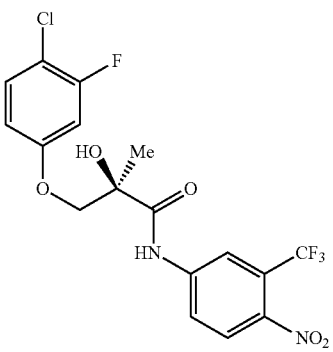

The compounds of the invention can contain a detectable element or a radiotherapeutic element in their structure. Detectable element is understood as any radioactive or fluorescent element, or positive contrast element for magnetic resonance imaging, preferably a metal ion, which displays a detectable property in an in vivo diagnostic technique. Radiotherapeutic element is understood as any element emitting α radiation, β radiation or, γ radiation.

The present invention relates to a method of treatment, prevention of clinical symptoms and/or diagnosis of lysosomal storage diseases and/or disorders and/or glycogenosis, which comprises the administration of a pharmaceutically effective amount of the compound (S)-bicalutamide and/or a structural analogue collectively defined by the general formula (I) or by the general formula (II), their pharmaceutically acceptable salts, their hydrates and/or their solvates.

The present invention relates to the use of the compound (S)-bicalutamide and/or a structural analogue collectively defined by the general formula (I) or by the general formula (II), their pharmaceutically acceptable salts, their hydrates and/or their solvates, in the preparation of a pharmaceutical composition for the diagnosis, prevention of the clinical symptoms, and/or treatment of lysosomal storage diseases and/or disorders and/or glycogenosis.

In a second aspect, the present invention relates to the compound (S)-bicalutamide and/or a structural analogue collectively defined by the general formula (I) or by the general formula (II), their pharmaceutically acceptable salts, their hydrates and/or their solvates for use in the diagnosis, prevention of clinical symptoms, and/or treatment of diseases and/or disorders which require stimulation of exocytosis, and more preferably, stimulation of lysosomal exocytosis.

The present invention also relates to a method of treatment, prevention of clinical symptoms and/or diagnosis of diseases and/or disorders which require stimulation of exocytosis, and more preferably stimulation of lysosomal exocytosis, which comprises the administration of a pharmaceutically effective amount of the compound (S)-bicalutamide and/or a structural analogue collectively defined by the general formula (I) or by the general formula (II), their pharmaceutically acceptable salts, their hydrates, and/or their solvates.

The present invention relates to the use of the compound (S)-bicalutamide and/or a structural analogue collectively defined by the general formula (I) or by the general formula (II), their pharmaceutically acceptable salts, their hydrates and/or their solvates, in the preparation of a pharmaceutical composition for the prevention of clinical symptoms and/or treatment of diseases and/or disorders which require stimulation of exocytosis, and more preferably stimulation of lysosomal exocitosis.

Compounds for use in the present invention can be administered in enantiomerically pure form or as an enantiomeric mixture, either as a racemic mixture or as mixtures containing an enantiomeric excess of any of both enantiomers. Preferably, the compounds for use in the present invention are in enantiomerically pure form or within mixtures with an enantiomeric excess higher than 99%, higher than 98%, higher than 97%, higher than 96%, higher than 95%, higher than 94%, higher than 93%, higher than 92%, higher than 91%, higher than 90%, higher than 85%, higher than 80%, higher than 75%, higher than 70%, higher than 65%, higher than 60%, higher than 55%, or higher than 50%.

Within the context of the present invention there are the pharmaceutically acceptable salts of the compounds for use in the invention. The term "pharmaceutically acceptable salts" refers to a salt recognised for its use in animals and more particularly in human beings, and includes salts used to form base addition salts, whether they are inorganic, for example and not restricted to, lithium, sodium, potassium, calcium, magnesium, manganese, copper, zinc or aluminium, amongst others, whether they are organic, for example and not restricted to, ethylamine, diethylamine, ethylenediamine, ethanolamine, diethanolamine, arginine, lysine, histidine or piperazine among others, or acid addition salts, whether they are organic, for example and not restricted to, acetate, citrate, lactate, malonate, maleate, tartrate, fumarate, benzoate, aspartate, diaspartate, triaspartate, glutamate, succinate, oleate, trifluoroacetate, oxalate, pamoate or gluconate amongst others, or inorganic, for example and not restricted to, chloride, sulfate, borate or carbonate amongst others. The nature of the salt is not critical, provided that it is pharmaceutically acceptable. The pharmaceutically acceptable salts of the compounds of the invention can be obtained by conventional methods that are well known in the state of the art [Berge S. M. et al., *Pharmaceutical salts. J. Pharm. Sci.* (1977), 66, 1-19].

In the context of the invention, the terms "lysosomal storage disease" and "lysosomal storage disorder" refer to diseases and/or disorders caused by or associated to the excessive and therefore pathologic storage of a compound in lysosomes. The terms "glycogen storage disorders" or "glycogenosis" refer to a group of diseases caused by an accumulation of glycogen due to a defect in the synthesis or degradation of glycogen, and therefore glycogen is accumulated in toxic amounts in cells. All the cells in the body can be affected by lysosomal storage diseases or glycogenosis. The person skilled in the art may know that a decrease in the toxic accumulation of substrates in the cell can lead to the treatment, prevention and/or relief of the clinical symptoms of many lysosomal storage diseases and/or glycogenosis. Lysosomal storage diseases and/or disorders include, but are not limited to, α-Mannosidosis, Aspartylglucosaminuria, β-Mannosidosis, Cystinosis, α-N-Acetylgalactosaminidase Deficiency (Schindler disease), Aspartoacylase or Aminoacylase Deficiency (Canavan disease), Multiple Sulfatase Deficiency (MSD), Steroid Sulfatase Deficiency, Cholesteryl ester storage disease, Wolman disease, Fabry disease, Farber disease, Gaucher disease (type I, II and III), Krabbe disease (including Infantile Onset, Late Onset, and activator deficiency), Niemann-Pick disease (type A/B and C), Fucosidosis, Galactosialidosis, GM1 Gangliosidosis (e.g. Infantile, Late Infantile/Juvenil and Adult/Chronic), GM2 Gangliosidosis (including the activator deficiency, Sandhoff disease and Tay-Sachs disease), Glycogenosis (e.g. Glycogenosis type I or Von Gierke disease, Glycogenosis type II or Pompe disease, Glycogenosis type IIb or Danon disease, Glycogenosis type V or McArdle disease and Glycogenosis type VII or Tarui disease), Metachromatic Leukodystrophy (including all its variants and due to the activator deficiency), Neuronal Ceroid Lipofuscinoses (including all their variants from NCL1 to NCL10), Mucolipidosis type I (Sialidosis, including all its variants such as the Infantile or Salla disease and the Juvenile), Mucolipidosis type II (I-Cell disease), Mucolipidosis type IIIA or α/β (Pseudo-Hurler polydystrophy), Mucolipidosis type IIIC or γ, Mucolipidosis type IV, Mucopolysaccharidoses type I (Hurler, Scheie and Hurler-Scheie syndromes), Mucopolysaccharidoses type II (Hunter syndrome), Mucopolysaccharidoses type III (Sanfilippo syndrome type A/MPS III A, Sanfilippo syndrome type B/MPS III B, Sanfilippo syndrome type C/MPS III C and Sanfilippo syndrome type D/MPS III D), Mucopolysaccharidoses type IV (Morquio type A/MPS IVA and Morquio type B/MPS IVB), Mucopolysaccharidoses type VI (Maroteaux-Lamy disease), Mucopolysaccharidoses type VII (Sly syndrome), Mucopolysaccharidoses type IX (Hyaluronidase Deficiency) and Pycnodysostosis.

Preferably, the lysosomal storage diseases and/or disorders are selected from, but not limited to, Sanfilippo syndrome type A, Sanfilippo syndrome type B, Hurler syndrome, Tay-Sachs disease, Gaucher disease, Fabry disease and Niemann-Pick disease type A/B.

In the context of the invention, the terms "exocytosis" or "cellular exocytosis" refer to the cellular process by which the cell, via an energy-dependent mechanism, directs the secretory vesicles out of the cell membrane, and release their content into the extracellular medium. More concretely, the term "lysosomal exocytosis" refers to those exocytosis processes where the exocytic vesicles are lysosomes.

In the context of the invention, the term "increase in lysosomal exocytosis" refers to an increase in lysosomal exocytosis compared to a reference, usually compared with the exocytosis value of a non-treated cell. In some embodiments, the treatment with the compound (S)-bicalutamide and/or a structural analogue collectively defined by the general formula (I) or by the general formula (II), their pharmaceutically acceptable salts, their hydrates and/or their solvates, leads to an increase in lysosomal exocytosis of at least 10%, at least 20%, at least 30%, at least 40%, at least 50%, at least 60%, at least 70%, at least 80%, at least 90%, or at least 95%, or is at least about the double, the triple, or even more compared with the value of a control not treated with said compound.

The increase in lysosomal exocytosis can be quantified by the person skilled in the art, for example in vitro, measuring the enzymatic activity of the β-hexosaminidase lysosomal enzyme in the culture medium [Xu M, et al, δ-*Tocopherol reduces lipid accumulation in Niemann-Pick type C1 and Wolman cholesterol storage disorders. J. Biol. Chem.* (2012) 287(47), 39349-39360]. In other embodiments, the increase in lysosomal exocytosis can be quantified by analysis of glycosaminoglycans decrease using the 1,9-dimethylmethylene blue (DMB) assay, adapted from Barbosa et al. [Barbosa et al., *Improved and simple micro assay for sulfated glycosaminoglycans quantification in biological extracts and its use in skin and muscle tissue studies. Glycobiology.* (2003), 13(9), 647-653]. In other embodiments, lysosomal exocytosis can also be observed by confocal microscopy, following the lysosomal movement by rabbit anti-LAMP1 selective labeling followed by incubation with the secondary antibody anti-rabbit linked to FITC [Medina D. L. et al., *Transcriptional activation of lysosomal exocytosis promotes cellular clearance. Dev. Cell.* (2011) 21(3), 421-430].

In the context of the invention, the term "decrease of glycosaminoglycanes (GAGs)" refers to the decrease in glycosaminoglycanes levels compared to a reference, the reference being usually the value of glycosaminoglycanes of an individual not treated with the compound. In some embodiments, the treatment of an individual with the compound (S)-bicalutamide and/or a structural analogue collectively defined by the general formula (I) or by the general formula (II), their pharmaceutically acceptable salts, their hydrates and/or their solvates, leads to a decrease in the glycosaminoglycans levels of at least 10%, at least 20%, at least 30%, at least 40%, at least 50%, at least 60%, at least 70%, at least 80%, at least 90%, or at least 95% compared with the value of a control not treated with said compound.

The "pharmaceutically effective amount" of (S)-bicalutamide and/or a structural analogue collectively defined by the general formula (I) or by the general formula (II), their pharmaceutically acceptable salts, their hydrates and/or their solvates, which should be administered, as well as their dosage, will depend on numerous factors, including age, state of the patient, the nature or severity of the disorder or disease to be treated or prevented, the route and frequency of administration, as well as on the specific nature of the compounds to be used.

"Pharmaceutically effective amount" is understood to mean a non-toxic but sufficient amount of a compound of the invention to provide the desired effect. The compounds of the invention are used in the pharmaceutically effective concentrations to achieve the desired effect. In each dose, the total amount of (S)-bicalutamide and/or a structural analogue collectively defined by the general formula (I) or by the general formula (II), their pharmaceutically acceptable salts, their hydrates and/or their solvates, that should be administered is effective to increase lysosomal exocytosis. Usually, the therapeutic dose of these compounds is in the range of 0.1 to 125 mg per Kg of body weight and per day, being the administered amount between 1 and 2000 mg per day. Preferably, the therapeutic dose is in the range of 0.5 to 100 mg/Kg, between 1 and 50 mg/Kg, between 5 and 25 mg/Kg, between 10 and 20 mg/Kg. Preferably, the amount of compound administered per day is between 0.1 and 2000 mg, between 0.5 and 1500 mg, between 1 and 1000 mg, between 5 and 750 mg, between 10 and 600 mg, between 20 and 400 mg, between 30 and 300 mg, and more preferably is 50, 100, or 150 mg.

Pharmaceutical Compositions and Combination Therapy

Thus, in another aspect, the invention relates to a pharmaceutical composition which comprises the compound (S)-bicalutamide and/or a structural analogue collectively defined by the general formula (I) or by the general formula (II), their pharmaceutically acceptable salts, their hydrates and/or their solvates, for the diagnosis, prevention of clinical symptoms, and/or treatment of lysosomal storage diseases and/or disorders and/or glycogenosis.

The pharmaceutical compositions for use in the present invention can comprise at least one pharmaceutically acceptable excipient. The number and nature of the pharmaceutically acceptable excipients depend on the desired route of administration. The pharmaceutically acceptable excipients are well known by the person skilled in the art [Rowe R. C., Sheskey P. J., Quinn, M. E. (2009) "*Handbook of Pharmaceutical Excipients, 6th Edition*", *Pharmaceutical Press and American Pharmacists Association*]. Said compositions may be prepared using conventional methods known in the state of the art.

The pharmaceutical compositions which contain the compound (S)-bicalutamide and/or a structural analogue collectively defined by the general formula (I) or by the general formula (II), their pharmaceutically acceptable salts, their hydrates and/or their solvates, may be administered via any appropriate route, for example topical, enteral, or parenteral route, and the pharmaceutically acceptable excipients necessary for the formulation by the desired administration route will be included. As is used herein, the term "topical" route includes dermal and ophthalmic routes, the term "enteral" route includes administration to the digestive system such as oral, buccal, gastric, sublingual and rectal routes, and the term "parenteral" refers to nasal, auricular, ophthalmic, vaginal, subcutaneous injections, intradermal, intravascular for example intravenous, intramuscular, intraocular, intraspinal, intracranial, intro-articular, intrathecal and intraperitoneal routes, as well as any other similar injection or infusion technique. Treatment in vitro is also considered, for example, by culture of the damaged cells and/or stem cells, and the ex vivo treatment. In a more preferred embodiment, the treatment is done in vivo, being the enteral route the preferred administration route.

The pharmaceutical compositions containing the compound (S)-bicalutamide and/or a structural analogue collectively defined by the general formula (I) or by the general formula (II), their pharmaceutically acceptable salts, their hydrates and/or their solvates, may be used in different types of formulations for their enteral administration, such as and not limited to, capsules, including gelatine capsules, soft capsules, hard capsules, tablets, including sugar coated tablets, pills, powders, granulated forms, chewing gums, solutions, suspensions, emulsions, syrups, elixirs, polysaccharide films, jelly or gelatins, as well as any other dosage form known in the state of the art. The compounds of the invention can be formulated with the usual excipients and adjuvants for oral compositions, such as and not limited to, fatty components, aqueous components, wetting agents, preservatives, texturing agents, flavours, aromas, antioxidants and colouring agents.

The compound (S)-bicalutamide and/or a structural analogue collectively defined by the general formula (I) or by the general formula (II), their pharmaceutically acceptable salts, their hydrates and/or their solvates, may also be incorporated into delivery systems and/or sustained release systems such as liposomes, milliparticles, microparticles and nanoparticles, sponges, vesicles, micelles, millispheres, microspheres and nanospheres, liposphers, millicapsules, microcapsules and nanocapsules, as well as microemulsions and nanoemulsions, which can be added to achieve a greater bioavailability of the active principle and/or improve its pharmacokinetic and pharmacodynamic properties. The sustained release formulations can be prepared by methods known in the state of the art, and can be administered, for example, by topical administration, including adhesive patches, oral, buccal, sublingual, gastric, rectal, intravenous, intramuscular or subcutaneous administration, or by direct implantation into a specific part of the body, and preferably should release a relatively constant amount of the compounds of the invention. The amount of compound contained in the sustained release formulation will depend on, for example, the administration site, the kinetics and duration of the release of the compound, as well as the nature of the condition to be treated or prevented.

The co-administration of the compound (S)-bicalutamide and/or a structural analogue collectively defined by the general formula (I) or by the general formula (II), their pharmaceutically acceptable salts, their hydrates and/or their solvates, in combination with other therapeutic active agents and pharmaceutical adjuvants can be done either in the same pharmaceutical composition, or in different pharmaceutical compositions. The combination can be done either in the same or in different pharmaceutical forms.

The compound (S)-bicalutamide and/or a structural analogue collectively defined by the general formula (I) or by the general formula (II), their pharmaceutically acceptable salts, their hydrates and/or their solvates, can be administered in combination with at least one adjuvant such as, but not limited to, other compounds that activate lysosomal exocytosis such as δ-tocopherol or cyclodextrins such as 2-hydroxypropyl-β-cyclodextrin, pharmacological chaperones that promote protein stabilization, compounds used in substrate reduction based therapies (SRT) such as N-butyl-deoxynojirimycin or miglustat (Zavesca®), migalastat hydrochloride or divoglustat hydrochloride, enzymes used in enzyme replacement therapies (ERT), antioxidant compounds, compounds used in gene therapy of lysosomal storage diseases and/or disorders and/or glycogenosis, and/or mixtures thereof.

The pharmaceutical compositions comprising the compound (S)-bicalutamide and/or a structural analogue collectively defined by the general formula (I) or by the general formula (II), their pharmaceutically acceptable salts, their hydrates and/or their solvates, can comprise at least one adjuvant such as, but not limited to, other compounds that activate lysosomal exocytosis such as δ-tocopherol or cyclodextrins such as 2-hydroxypropyl-β-cyclodextrin, pharmacological chaperones that promote protein stabilization, compounds used in substrate reduction based therapies (SRT) such as N-butyl-deoxynojirimycin or miglustat (Zavesca®), migalastat hydrochloride or divoglustat hydrochloride, enzymes used in enzyme replacement therapies (ERT), antioxidant compounds, compounds used in gene therapy of lysosomal storage diseases and/or disorders and/or glycogenosis, and/or mixtures thereof.

Examples of pharmacological chaperones include, but are not limited to, 1-deoxynojirimycin, nojirimycin-1-sulfonic acid, N-(7-oxadecyl)-1-deoxynojirimycin, 2-acetamido-deoxynojirimycin, 2-acetamido-1,2-dideoxynojirimycin, 1-deoxygalactonojirimycin, N-butyl-deoxygalactonojirimycin, castanospermine, N-acetylglucosamine thiazoline, galactose, nitroindanone, pyrimethamine, miglustat, migalastat hydrochloride, divoglustat hydrochloride, 2,5-dideoxy-2,5-imino-D-altritol, isofagomine, ambroxol, diltiazem, glucosamine, their structural analogues, their salts and/or mixtures thereof.

Examples of enzymes used in enzyme replacement therapies (ERT) include, but are not limited to, natural enzymes and/or their recombinant synthetic forms and/or their synthetic recombinant mutants of N-aspartyl-β-glucosaminidase, acetyl-CoA α-glucosaminide N-acetyltransferase, N-acetylglucosamine-6-sulfatase, N-acetylglucosamine-1-phosphotransferase, α-N-acetylglucosaminidase, α-N-acetylneuraminidase, sialidase, acid ceramidase, acid α-glucosidase, acid maltase, aspartoacylase, lysosomal lipase acid, acid sphingomyelinase, arylsulfatase A, arylsulfatase B, α-L-fucosidase, galactocerebrosidase, galactosamine-6-sulfatase, α-galactosidase A, α-galactosidase B, β-galactosidase, galactosylceramidase, β-glucoronidase, β-glucosidase, β-glucocerebrosidase, heparan N-sulfatase, β-hexosaminidase A, β-hexosaminidase NB, hyaluronidase-1, α-L-iduronidase, iduronate-2-sulfatase, α-D-mannosidase, β-mannosidase and α-neuraminidase, and/or mixtures thereof. Some of these enzymes are commercially available, such as Fabrazyme®, Replagal®, VPRIV®, Cerezyme®, Ceredase®, ELELYSO™, UPLYSO™, Aldurazyme®, Elaprase®, Naglazyme®, Lumizyme®, or Myozyme®.

Examples of antioxidant compounds include, but are not limited to, some vitamins and their derivatives such as Vitamin A or retinol, such as retinyl palmitate and retinyl acetate, Vitamin C or ascorbic acid, such as ascorbyl palmitate and ascorbyl acetate, or Vitamin E, including tocotrienol and tocopherols, such as tocopherol acetate; vitamin cofactors and minerals such as coenzyme Q10, manganese or iodide; idebenone; some hormones such as melatonine; carotenoid terpenoids such as α-carotene, astaxanthine, β-carotene, cantaxanthine, lutein, licopen or zeaxanthine; flavones such as apigenin, luteolin or tangeritin; flavonols such as isoramnetine, kaempferol, myricetin, proanthocyanidins, quercetin or rutin; flavanones such as eriodictyol, hesperetin or naringenin; flavanols and their polymers such as catechin, gallocatechin, epicatechin, epigallocatechin, theaflavin or thearubigin; phytoestrogens, isoflavones such as daidzein, genistein or glycitein; stilbenoids such as resveratrol or pterostilbene; anthocyanins such as cyanidin, delphinidin, malvidin, pelargonidin, peonidin or petunidin; phenolic acids and their esters, such as cichoric acid, chlorogenic acid, cinnamic acid, ferulic acid, ellagic acid, ellagitannin, gallic acid, gallotannins, rosmarinic acid or salicylic acid; flavonolignans such as silymarin; xanthones or eugenol; other organic antioxidants such as capsaicin, bilirubin, citric acid, oxalic acid, phytic acid, N-acetylcysteine, R-α-lipoic acid, uric acid, carnosin and their derivatives; carnitin and their derivatives, Lipochroman-6 (Dimethylmethoxy Chromanol), Trolox (6-hydroxy-2,5,7,8-tetramethylchroman-2-carboxylic acid), tert-butylhydroquinone (TBHQ) and/or mixtures thereof.

In another particular embodiment, the compound (S)-bicalutamide and/or a structural analogue collectively defined by the general formula (I) or by the general formula (II), their pharmaceutically acceptable salts, their hydrates and/or their solvates, can be coadministered together with other pharmaceutical actives and/or adjuvants. In particular, the pharmaceutical actives and/or adjuvants are selected, but not limited to, the group comprising antiacids, agents against peptic ulcers and gastroesophageal reflux disease, antispasmodics, analgesics, anticholinergic drugs, propulsive drugs, antiemetics, antinausea drugs, agents for biliary therapy, agents for hepatic therapy, lipotropics, laxatives, antidiarrhetics, intestinal adsorbents, antipropulsives, anti-inflammatory drugs, active ingredients against obesity, enzymes, hypoglycemic drugs, insulin and analogues, vitamins, proteins, minerals, anabolic steroids, antithrombotic agents, antifibrinolytics, haemostatic agents, antiarrhythmic agents, cardiac stimulants, cardiac glycosides, vasodilators, antiadrenergic agents, antihypertensive drugs, diuretics, potassium-saving agents, antihemorrhoidals, antivaricose therapy agents, capillary stabilizing agents, agents which act on the renin-angiotensin system, beta-blockers, selective calcium channel blockers, non-selective calcium channel blockers, ACE inhibitors, angiotensin II inhibitors, lipid modifying agents, antifungals, healing agents, antipruritics, antihistamines, anesthetics, antipsoriatics, chemotherapy drugs, corticosteroids, antiseptics, disinfectants, anti-acne agents, products for gynecological use, oxytocics, anticonceptives, androgen, estrogen, progestagen, ovulation stimulants, gonadotropins, antiandrogens, products for urological use, antispasmodics, drugs used in benign prostatic hypertrophy, hormones, hormone antagonists, antibiotics, tetracyclines, amphenicols, beta-lactam antibacterials, penicillin, sulfonamides, trimethoprim, macrolides, lincosamides, streptogramins, antibacterial aminoglycosides, antibacterial quinolones, antivirals, immune serum, immunoglobulins, antineoplastic agents, immunomodulatory agents, alkylating agents, antimetabolites, plant alkaloids and other natural products, cytotoxic antibiotics, immunosuppressive agents, drugs for disorders of the musculoskeletal system, antirheumatics, muscle relaxant agents, agents which affect bone structure and mineralization, drugs acting on the nervous system, general anesthetics, local anesthetics, opioids, antimigraine agents, anticonvulsants, anticholinergic agents, dopaminergic agents, antipsychotics, anxiolytics, hypnotics, sedatives, antidepressants, psychostimulants, anti-dementia drugs, parasympathomimetics, drugs used in addictive disorders, anti-vertigo agents, antiparasitic agents, insecticides, insect repellants, nasal decongestants, mucolytic agents, cough suppressants, ophthalmic active ingredients, otological active ingredients, antiglaucoma drugs, miotics, mydriatics, cycloplegics and/or mixtures thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1. Confocal microscopy images of skin derived fibroblasts from a patient affected by Sanfilippo B disease and control fibroblasts from a healthy individual treated with a lysosomal antibody anti-LAMP-1.

EXAMPLES

The following specific examples provided here illustrate the nature of the present invention. These examples are only included for illustrative purposes and should not be interpreted as limitations to the invention claimed herein Experimental Procedures Fibroblasts Culture.

Fibroblasts from thirteen patients affected by seven different lysosomal storage diseases (Fabry, Gaucher, Hurler, Niemann-Pick type A/B, Sanfilippo A, Sanfilippo B and Tay-Sachs) were cultured in DMEM (Dulbecco's modified Eagles medium) with 10% fetal bovine serum and in the presence of antibiotics (penicillin and streptomycin), at 37° C. with 5% $CO_2$. All reagents were purchased from PAA Laboratories (Velizy-Villacoublay, France). The fibroblasts of the patients were selected on the basis of availability of fibroblasts and measurable residual activity. The use of human samples was approved by the Ethical Committee of Hospital Clinic, Barcelona Treatment and Determination of Cell Viability.

Fibroblasts of early passage (between 5 and 9 passages) were plated in 6- or 24-well plates depending on the test and were treated for 72 hours with increasing concentrations (10 nmol/L, 100 nmol/L, 1 µmol/L, 10 µmol/L, 50 µmol/L and 100 µmol/L) of bicalutamide (Sigma-Aldrich, St. Louis, USA) and (R)- and (S)-bicalutamide (Toronto Research Chemicals Inc., Toronto (Ontario), Canada). Cell viability was evaluated in each cell line for each concentration using the 3-[4,5-dimethylthiazol-2-yl]-2,5-diphenyl tetrazolium bromide (MTT) assay (Sigma-aldrich, St. Louis, USA) described by Sumantran V. N. *Cellular chemosensitivity assays: an overview.* Methods Mol. Biol. (2011), 731, 219-236.

Enzymatic Activities.

Fibroblasts cultured for 72 h in 24 well-plates in the presence or absence of bicalutamide, (S)-bicalutamide, (S)-bicalutamide analogs or (R)-bicalutamide at different concentrations in triplicate (10 nmol/L, 100 nmol/L, 1 µmol/L, 10 µmol/L, 50 µmol/L and 100 µmol/L), were rinsed with physiological saline. The cells were lysed by using 3 freeze-thaw cycles. Then protein concentration was determined by using the Lowry method. Protein lysates (10 µg) were seeded in 96-well plates and the enzymatic activity of the enzyme involved in each disease was determined in triplicate by means of fluorimetric artificial substrates: 4-methylumbelliferyl-α-N-sulphoglucosaminide for Sanfilippo A, 4-methylumbelliferyl-2-acetamido-2 deoxy-α-D-glucopyranoside for Sanfilippo B, 4-methylumbelliferyl-α-L-iduronide for Hurler, 4-methylumbelliferyl-N-acetyl-β-D-glucosaminide for Tay-sachs, 4-methylumbelliferyl-β-D-glucopyranoside for Gaucher, 4-methylumbelliferyl-α-Galactopiranosid for Fabry disease, and 6-hexadecanoylamino-4-methylumbelliferyl-P-colline for Niemann-Pick type AB. The activity of the enzyme β-hexosaminidase was assayed by using 4-methylumbelliferyl-2 acetamido-2 deoxy-β-D-glucopyranoside as artificial substrate [Annunziata et al., *Study of influence of sex and age on human serum lysosomal enzymes by using 4-methylumbelliferyl substrates.* Clin. Chim. Acta. (1978), 90(2), 101-106].

Determination of Lysosomal Exocytosis.

Lysosomal exocytosis was monitorized by measuring the enzymatic activity of the lysosomal enzyme β-hexosaminidase in the culture medium [Xu M, et al, δ-*Tocopherol reduces lipid accumulation in Niemann-Pick type C1 and Wolman cholesterol storage disorders.* J. Biol. Chem. (2012) 287(47), 39349-39360]. The fibroblasts were previously treated with different concentrations of bicalutamide, (S)-bicalutamide or (R)-bicalutamide (10 nmol/L, 100 nmol/L, 1 µmol/L, 10 µmol/L, 50 µmol/L and 100 µmol/L) in triplicate in 24-well plates. At 0, 24, 48 and 72 hours, 30 µL of culture medium was aliquoted for the subsequent β-hexosaminidase activity assay.

Analysis of LAMP1 in the Surface as an Exocytosis Marker.

Fibroblasts samples were cultured on coverslips and treated with a 50 µM solution of bicalutamide, (S)-bicalutamide, (S)-bicalutamide analogs or (R)-bicalutamide for 24 and 48 hours. Then, the cells were incubated with rabbit anti-LAMP1 for 30 min at 4° C. They were then washed with PBS and fixed with 2% paraformaldehyde. Cells treated with anti-LAMP1 were incubated with a secondary antibody anti-rabbit bound to fluorescein (FITC) for 30 min at room temperature [Medina D. L. et al., *Transcriptional activation of lysosomal exocytosis promotes cellular clearance.* Dev. Cell. (2011) 21(3), 421-430]. Finally, the cells were observed on a confocal microscope (Leica TCS-NT).

Determination of Glycosaminoglycans (GAGs).

GAGs quantification was performed by using the 1,9-dimethylmethylene blue (DMB) assay adapted from Barbosa et al (2003) [Barbosa et al., *Improved and simple micro assay for sulphated glycosaminoglycans quantification in biological extracts and its use in skin and muscle tissue studies.* Glycobiology. (2003), 13(9), 647-653]. The fibroblasts were cultured in triplicate in 6-well plates and they were harvested 72 hours after treatment. DMB absorbance was measured in duplicate at 656 nm with a microplate reader (POLARstar Omega, BMG LABTECH, Offenburg, Germany).

Abbreviations

The abbreviations used in the present description have the following meanings:

Ac, acetyl; Br, bromine; Cl, chlorine; $CF_3$; trifluorometthyl; CN, nitrile; $CO_2$, carbon dioxide; DMEM, Dulbecco's modified Eagles medium; DMB, 1,9-dimethylmethylene blue; F, fluorine; FITC, fluorescein isothiocyanate; GAGs, glycosaminoglicanes; I, iodine; Kg, kilogram; L, liter; LAMP1, lysosomal-associated membrane protein 1; mg, milligram; MTT, 3-[4,5-dimethylthiazol-2-yl]-2,5-diphenyl tetrazolium bromide; nmol, nanomol; $NO_2$, nitro; —NHAc, acetamido; —$NAc_2$, N,N-diacetamido; PBS, phosphate buffer saline; SCN—, isothiocyanate; µg, microgram; µL, microliter; µM, micromolar; µmol, micromol;

Example 1

Increase in Lysosomal Exocytosis in Fibroblasts of Patients Affected by Different Lysosomal Storage Diseases after Treatment with Bicalutamide (Racemic Mixture)

Fibroblasts from two patients affected by Sanfilippo B and Hurler diseases were treated with different concentrations of bicalutamide (racemic mixture at increasing concentrations of 0.01, 0.1, 1, 10 and 100 μM). And the increase in lysosomal exocytosis was determined by analyzing the enzymatic activity of the lysosomal enzyme β-hexosaminidase in the culture medium. The results, expressed as percentage increase relative to the activity values obtained for untreated fibroblasts, showed an increased enzymatic activity in the culture medium of between 23 to 100% in fibroblasts of a patient affected by Sanfilippo B disease and of between 3 to 14% in fibroblasts of a patient affected by Hurler disease. The treatment with bicalutamide increases the activity of the lysosomal enzyme β-hexosaminidase in the culture medium, indicating therefore an increase in lysosomal exocytosis.

TABLE 1

Percentage increase in lysosomal exocytosis in fibroblasts from two patients affected by Sanfilippo B and Hurler diseases treated with different concentrations of racemic bicalutamide.

| | | Increase in lysosomal Exocytosis (%) Concentration of Racemic Bicalutamide | | | | | |
|---|---|---|---|---|---|---|---|
| Patient | Disease | Untreated | 10 nM | 100 nM | 1 μM | 10 μM | 100 μM |
| 1 | Sanfilippo B | 0 | 31* | 23* | 49 | 45 | 100* |
| 2 | Hurler | 0 | 14 | 13 | 9 | 3 | 8 |
| 3 | Control | 0 | 0 | 27 | 13 | 12* | 13* |

*p < 0.05.

Example 2

Decrease of Glycosaminoglycans (GAGs) in Fibroblasts from Different Patients Affected by Several Lysosomal Storage Diseases Treated with Bicalutamide (Racemic Mixture)

Fibroblasts from three patients affected by Sanfilippo B disease and one patient affected by Hurler disease were treated with increasing concentrations of bicalutamide (racemic mixture at increasing concentrations of 0.01, 0.1, 1, 10 and 100 μM). Glycosaminoglycans (GAGs) levels were quantified with the 1,9-dimethylmethylene blue (DMB) assay. The results, expressed as percentage decrease relative to the activity value obtained for untreated fibroblasts, showed a decreased GAGs accumulation in the fibroblasts of the three patients affected by Sanfilippo B disease treated with bicalutamide, of between 17 and 54% in the first patient, of between 16 and 20% in the second patient and of between 13 and 53% in the third patient. GAGs were not detected in the fibroblasts of a patient affected by Hurler disease. Thus, the treatment with bicalutamide of fibroblasts of different patients affected by several lysosomal storage diseases reduces the levels of accumulated GAGs, revealing an increase in exocytosis.

TABLE 2

Percentage decrease of GAGs in fibroblasts from two patients affected by Sanfilippo B (3 different patients) and Hurler (1 patient) diseases treated with different concentrations of racemic bicalutamide.

| | | Decrease of GAGs (%) Concentration of Racemic Bicalutamide | | | | | |
|---|---|---|---|---|---|---|---|
| Patient | Disease | Untreated | 10 nM | 100 nM | 1 μM | 10 μM | 100 μM |
| 1 | Sanfilippo B | 0 | 17 | 25 | 17 | 22* | 54* |
| 2 | Sanfilippo B | 0 | 0 | 16 | 0 | 0 | 20 |
| 3 | Sanfilippo B | 0 | 53 | 13 | 33 | 33 | 0 |
| 4 | Hurler | 0 | 0 | 0 | 0 | 0 | 0 |
| 5 | Control | 0 | 0 | 0 | 0 | 0 | 0 |

*p < 0.05.

Example 3

Cell Viability of Fibroblasts from Nine Patients Affected by Different Lysosomal Storage Diseases Treated with Enantiomerically Pure Bicalutamide Comparison of the Efficacy of the Two Enantiomers Fibroblasts from thirteen patients with different lysosomal storage diseases (four patients affected by Sanfilippo B disease patients with different genotypes, three Sanfilippo A disease patients with different genotypes, two Tay-Sachs disease patients with the same genotype, one Gaucher disease patient, one Niemann-PickA/B disease patient, one Hurler disease patient and one Fabry disease patient) were independently treated with different concentrations of (R)- and (S)-bicalutamide (50 and 100 μM). Cell viability was evaluated for each treatment in each cell line using the MTT assay. Five of the patient's fibroblast cultures treated with (R)-bicalutamide showed a significant decrease in their cell viability (of between 10 and 52%). In contrast, treatment with (S)-bicalutamide in the thirteen fibroblasts cultures did not show any significant decrease of cell viability, indicating the higher toxicity of the enantiomer (R) and a non-toxic effect of the enantiomer (S).

TABLE 3

Percentage decrease of cell viability in fibroblasts from nine patients affected by different lysosomal storage diseases independently treated with different concentrations of (R)- and (S)-bicalutamide for 72 h.

| | | Decrease of Cell Viability (%) | | | |
|---|---|---|---|---|---|
| | | (R)-BICALUTAMIDE (2) | | (S)-BICALUTAMIDE (1) | |
| Patient | Disease | 50 μM | 100 μM | 50 μM | 100 μM |
| 1 | Sanfilippo B | 20* | 37* | 0 | 0 |
| 2 | Sanfilippo B | 10* | 26* | 0 | 0 |
| 3 | Sanfilippo B | 40* | 52* | 0 | 0 |
| 4 | Sanfilippo B | 0 | 25* | 0 | N.S. |
| 5 | Sanfilippo A | N.S. | N.S. | 0 | 0 |
| 6 | Sanfilippo A | 0 | 0 | 0 | 0 |
| 7 | Sanfilippo A | 0 | 0 | 0 | 0 |
| 8 | Tay-Sachs | 0 | 0 | 0 | 0 |
| 9 | Tay-Sachs | 0 | N.S. | 0 | N.S. |
| 10 | Gaucher | 0 | 24* | N.S. | N.S. |
| 11 | Niemann-Pick AB | 0 | 0 | N.S. | N.S. |
| 12 | Hurler | 0 | 0 | 0 | 0 |
| 13 | Fabry | 0 | 0 | 0 | 0 |

*$p < 0.05$.
N.S.: non significant decrease.

Example 4

Increase in Exocytosis in Fibroblasts from Patients Affected by Different Lysosomal Storage Diseases Treated with Enantiomerically Pure Bicalutamide Comparison of the Efficacy of Both Enantiomers Fibroblasts from thirteen patients affected by different lysosomal storage diseases (four Sanfilippo B disease patients with different genotypes, three Sanfilippo A disease patients with different genotypes, two Tay-Sachs disease patients with the same genotype, one Gaucher disease patient, one Niemann-pick type A/B disease patient, one Hurler disease patient, and one Fabry disease patient) were independently treated with different concentrations of (R)- and (S)-bicalutamide (50 and 100 μM) for 72 hours. Results show that (S)-bicalutamide is able to significantly increase lysosomal exocytosis in ten of the thirteen cell cultures treated, while (R)-bicalutamide was only able to significantly increase lysosomal exocytosis in one of the tested cell cultures. Treatment with (S)-bicalutamide is more effective and universal than treatment with (R)-bicalutamide. Fibroblasts treated with (S)-bicalutamide showed an increase in the exocytosis at 72 h in a significant and dose-dependent manner. Treatment with (R)-bicalutamide resulted in some increase in exocytosis, but neither dose-dependent nor statistically significant (table 4).

TABLE 4

Percentage increase in lysosomal exocytosis in fibroblasts from nine patients affected by different lysosomal storage diseases and independently treated with different concentrations of (R)- and (S)-bicalutamide for 72 h.

| | | Increase in exocytosis (%) | | | |
|---|---|---|---|---|---|
| | | (R)-BICALUTAMIDE (2) | | (S)-BICALUTAMIDE (1) | |
| Patient | Disease | 50 μM | 100 μM | 50 μM | 100 μM |
| 1 | Sanfilippo B | 0 | 257* | N.S. | N.S. |
| 2 | Sanfilippo B | N.S. | N.S. | N.S. | 166* |
| 3 | Sanfilippo B | N.S. | N.S. | N.S. | N.S. |
| 4 | Sanfilippo B | N.S. | 0 | 33* | 28* |
| 5 | Sanfilippo A | 0 | 0 | 72* | 39* |
| 6 | Sanfilippo A | N.S. | N.S. | 70* | 64* |
| 7 | Sanfilippo A | N.S. | 0 | 121* | 109* |
| 8 | Tay-Sachs | N.S. | 0 | N.S. | 127* |
| 9 | Tay-Sachs | N.S. | 0 | N.S. | 124* |
| 10 | Gaucher | N.S. | 0 | N.S. | N.S. |
| 11 | Niemann-Pick AB | N.S. | 0 | 114* | 60* |
| 12 | Hurler | N.S. | N.S. | 13629* | 5949* |
| 13 | Fabry | N.S. | 0 | 5402* | 3432* |
| | Median | 0 | 0 | 114* | 124* |

*$p < 0.05$.
N.S.: non significant increase.

Example 5

Decrease of Glycosaminoglicans (GAGs) in Fibroblasts from Nine Different Patients Affected by Different Lysosomal Storage Diseases Treated with Enantiomerically Pure Bicalutamide Comparison of the Activity of Both Enantiomers Fibroblasts from seven patients affected by different diseases derived from lysosomal storage (three Sanfilippo B disease patients with different genotypes, one Sanfilippo A disease patient, one Tay-Sachs disease patient, one Niemann-Pick type A/B disease patient and one Hurler disease patient) were independently treated with different concentrations of (R)- and (S)-bicalutamide (50 and 100 µM). Fibroblasts treated with the (S) enantiomer showed a significant and dose-dependent decrease of glycoaminoglicans, reaching this reduction in GAGS levels control levels. Results with the (R) enantiomer, showed a decrease of GAGs levels in some cases, but with a lower intensity and not universally, in contrast to the treatment with the (S) enantiomer (table 5).

TABLE 5

Percentage decrease of GAGs in fibroblasts from nine patients affected by different lysosomal storage diseases treated independently with different concentrations of (R)- and (S)-bicalutamide for 72 h.

| | | Decrease of GAGs (%) | | | |
|---|---|---|---|---|---|
| | | (R)-BICALUTAMIDE (2) | | (S)-BICALUTAMIDE(1) | |
| Patient | Disease | 50 µM | 100 µM | 50 µM | 100 µM |
| 1 | Sanfilippo B | N.S. | 25* | N.S. | 22* |
| 2 | Sanfilippo B | N.S. | N.S. | 18* | 39* |
| 3 | Sanfilippo B | 0 | 33* | 15* | 20* |
| 4 | Sanfilippo A | 0 | 0 | 27.4* | 56* |
| 5 | Tay-Sachs | N.S. | 45* | 31* | 60* |
| 6 | Niemann-Pick AB | N.S. | 41* | 24* | 38* |
| 7 | Hurler | 0 | 16* | 0 | 0 |
| | Median | 0 | 25* | 18* | 38* |

*p < 0.05.
N.S.: no significant increase.

Example 6

Analysis of LAMP1 on the Surface as a Marker of Exocytosis in Fibroblasts Treated with Bicalutamide Fibroblasts from a patient affected by Sanfilippo B disease (p. [Y658F]+[Y658F]) and control fibroblasts from a healthy patient were seeded on coverslips and treated with 50 µM of bicalutamide. Fibroblasts were incubated with rabbit anti-LAMP1 for 30 minutes at 4° C. Afterwards they were washed with PBS and fixed with 2% paraformaldehyde. The fibroblasts treated with anti-LAMP1 were incubated with a secondary antibody anti-LAMP1 linked to FITC for 30 minutes at room temperature and they were observed in a confocal microscope. As it is shown in FIG. 1 the treatment with racemic bicalutamide increases the fusion of the lysosome with the plasma membrane revealing an increase in exocytosis.

The invention claimed is:

1. A method of treating and/or preventing clinical symptoms associated with a lysosomal storage disease, a lysosomal storage disorder, a glycogenosis, or a combination thereof in a subject in need thereof, the method comprising administering to the subject a pharmaceutically effective amount of (S)-bicalutamide (1),

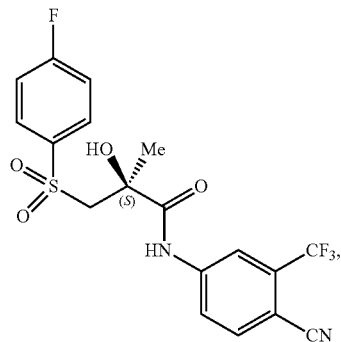

(1)

and/or a pharmaceutically acceptable salt, hydrate and/or a solvate thereof, in an enantiomerically pure form or having an enantiomeric excess of the (S) enantiomer higher than 95%, and wherein the amount of the (R) enantiomer is lower than 2.5%.

2. The method according to claim 1, wherein the lysosomal storage disease, the lysosomal storage disorder, the glycogenosis, or the combination thereof is selected from the group consisting of α-Mannosidosis, Aspartylglucosaminuria, β-Mannosidosis, Cystinosis, α-N-Acetylgalactosaminidase Deficiency or Schindler disease, Aspartoacylase Deficiency, Aminoacylase Deficiency or Canavan disease, Multiple Sulfatase Deficiency or MSD, Steroid Sulfatase Deficiency, Cholesteryl ester storage disease, Wolman disease, Fabry disease, Farber disease, Gaucher disease, Krabbe disease, Niemann-Pick disease, Fucosidosis, Galactosialidosis, GM1 Gangliosidosis, GM2 Gangliosidosis, Glycogenosis type I or Von Gierke disease, Glycogenosis type II or Pompe disease, Glycogenosis type IIb or Danon disease, Glycogenosis type V or McArdle disease, Glycogenosis type VII or Tarui disease, Metachromatic Leukodystrophy, Neuronal Ceroid Lipofuscinoses, Mucolipidosis type I or Sialidosis, Mucolipidosis type II or I-Cell disease, Mucolipidosis type IIIA or α/β, Pseudo-Hurler polydystrophy, Mucolipidosis type IIIC or γ, Mucolipidosis type IV, Mucopolysaccharidoses type I, Mucopolysaccharidoses type II or Hunter syndrome, Mucopolysaccharidoses type III, Mucopolysaccharidoses type IV, Mucopolysaccharidoses type VI or Maroteaux-Lamy disease, Mucopolysaccharidoses type VII or Sly syndrome, Mucopolysaccharidoses type IX by Hyaluronidase Deficiency, and Pycnodysostosis.

3. The method according to claim 1, wherein the (S)-bicalutamide and/or the pharmaceutically acceptable salt, hydrate and/or solvate thereof is administered in an amount ranging from 0.1 to 2000 mg per day.

4. The method according to claim 1, further comprising administering to the subject at least one adjuvant selected from the group consisting of compounds that activate lysosomal exocytosis, pharmacological chaperones that promote protein stabilization, compounds used in substrate reduction therapies (SRT), enzymes used in enzyme replacement therapies (ERT), antioxidant compounds, compounds used in gene therapy of a lysosomal storage disease, a lysosomal storage disorder, glycogenosis, or combination thereof.

5. The method according to claim 4, wherein the adjuvant is a compound that activates lysosomal exocytosis selected from the group consisting of δ-tocopherol, 2-hydroxypropyl-β-cyclodextrin, and/or mixtures thereof.

6. The method according to claim 4, wherein the adjuvant is a compound used in substrate reduction therapy selected from the group consisting of N-butyl-deoxynojirimycin or miglustat, migalastat hydrochloride, divoglustat hydrochloride, and/or mixtures thereof.

7. The method according to claim 4, wherein the adjuvant is a enzyme used in enzyme replacement therapy selected from the group consisting of natural enzymes and/or their recombinant synthetic forms and/or their recombinant synthetic mutants of N-aspartyl-β-glucosaminidase, acetyl-CoA α-glucosaminide N-acetyltransferase, N-acetylglucosamine-6-sulfatase, N-acetylglucosamine-1-phosphotransferase, α-N-acetylglucosaminidase, α-N-acetylneuraminidase, sialidase, acid ceramidase, acid α-glucosidase, acid maltase, aspartoacylase, lysosomal lipase acid, acid sphingomyelinase, arylsulfatase A, arylsulfatase B, α-L-fucosidase, galactocerebrosidase, galactosamine-6-sulfatase, α-galactosidase A, α-galactosidase B, β-galactosidase, galactosylceramidase, β-glucoronidase, β-glucosidase, β-glucocerebrosidase, heparan N-sulfatase, β-hexosaminidase A, β-hexosaminidase A/B, hyaluronidase-1, α-L-iduronidase, iduronate-2-sulfatase, α-D-mannosidase, β-mannosidase and α-neuraminidase, and/or mixtures thereof.

8. The method according to claim 4, wherein the adjuvant is a pharmacological chaperone selected from the group consisting of 1-deoxynojirimycin, nojirimycin-1-sulfonic acid, N-(7-oxadecyl)-1-deoxynojirimycin, 2-acetamido-deoxynojirimycin, 2-acetamido-1,2-dideoxynojirimycin, 1-deoxygalactonojirimycin, N-butyl-deoxygalactonojirimycin, castanospermine, N-acetylglucosamine thiazoline, galactose, nitroindanone, pyrimethamine, miglustat, migalastat hydrochloride, divoglustat hydrochloride, 2,5-dideoxy-2,5-imino-D-altritol, isofagomine, ambroxol, diltiazem, glucosamine, their structural analogues, their salts and/or mixtures thereof.

9. The method according to claim 4, wherein the adjuvant is an antioxidant compound selected from the group consisting of Vitamin A or retinol, Vitamin C or ascorbic acid, Vitamin E, tocotrienol and tocopherols, coenzyme Q10, manganese, iodide, idebenone, melatonine, α-carotene, astaxanthine, β-carotene, cantaxanthine, lutein, licopen, zeaxanthine, flavones, apigenin, luteolin, tangeritin, flavonols, isoramnetine, kaempferol, myricetin, proanthocyanidins, quercetin, rutin, flavanones, eriodictyol, hesperetin, naringenin, flavanols and their polymers, catechin, gallocatechin, epicatechin, epigallocatechin, theaflavin, thearubigin, phytoestrogens, isoflavones, daidzein, genistein, glycitein, stilbenoids, resveratrol, pterostilbene, anthocyanins, cyanidin, delphinidin, malvidin, pelargonidin, peonidin, petunidin, phenolic acids and their esters, cichoric acid, chlorogenic acid, cinnamic acid, ferulic acid, ellagic acid, ellagitannin, gallic acid, gallotannins, rosmarinic acid, salicylic acid, flavonolignans, silymarin, xanthones, eugenol, capsaicin, bilirubin, citric acid, oxalic acid, phytic acid, N-acetylcysteine, R-α-lipoic acid, uric acid, carnosin and their derivatives, carnitin and their derivatives, Lipochroman-6 (Dimethylmethoxy Chromanol), Trolox (6-hydroxy-2,5,7,8-tetramethylchroman-2-carboxylic acid), tert-butylhydroquinone (TBHQ) and/or mixtures thereof.

10. A method of treating and/or preventing clinical symptoms associated with a lysosomal storage disease, a lysosomal storage disorder, glycogenosis, or combination thereof in a subject in need thereof, the method comprising administering to the subject a pharmaceutical composition comprising (S)-bicalutamide and/or a pharmaceutically acceptable salt, hydrate and/or solvate thereof, in an enantiomerically pure form or having an enantiomeric excess of the (S) enantiomer higher than 95%, and wherein the amount of the (R) enantiomer is lower than 2.5%.

11. The method according to claim 10, wherein the (S)-bicalutamide and/or the pharmaceutically acceptable salt, hydrate and/or solvate thereof is incorporated into a delivery system and/or sustained release system selected from the group consisting of liposomes, milliparticles, microparticles, nanoparticles, sponges, vesicles, micelles, millispheres, microspheres, nanospheres, liposheres, millicapsules, microcapsules, nanocapsules, microemulsions and nanoemulsions.

12. The method according to claim 10, wherein the pharmaceutical composition further comprises at least one adjuvant selected from the group consisting of compounds that activate lysosomal exocytosis, pharmacological chaperones that promote protein stabilization, compounds used in substrate reduction based therapies (SRT), enzymes used in enzyme replacement therapies (ERT), antioxidant compounds, and/or compounds used in gene therapy of a lysosomal storage disease, a lysosomal storage disorder, glycogenosis, or combination thereof.

13. The method according to claim 10, wherein the administering is performed by a topical, an enteral or a parenteral route.

14. The method according to claim 2, wherein the Mucopolysaccharidoses type III is Sanfilippo syndrome type A/MPS III A, Sanfilippo syndrome type B/MPS III B, Sanfilippo syndrome type C/MPS III C or Sanfilippo syndrome type D/MPS III D.

15. The method according to claim 2, wherein the Mucopolysaccharidoses type I is Hurler, Scheie or Hurler-Scheie syndrome.

16. The method according to claim 2, wherein the Mucopolysaccharidoses type IV is Morquio type A/MPS IVA or Morquio type B/MPS IVB.

17. The method according to claim 2, wherein the Niemann-Pick disease is Niemann-Pick disease type A/B or Niemann-Pick disease type C.

18. The method according to claim 2, wherein the GM2 Gangliosidosis is the activator deficiency variant, Sandhoff disease or Tay-Sachs disease.

19. The method according to claim 1, wherein the lysosomal storage disease, lysosomal storage disorder, glycogenosis, or a combination thereof is selected from the group consisting of Sanfilippo syndrome type A, Sanfilippo syndrome type B, Hurler syndrome, Tay-Sachs disease, Gaucher disease, Fabry disease, Pompe disease and Niemann-Pick disease type A/B.

20. The method according to claim 2, wherein the lysosomal storage disease, the lysosomal storage disorder, the glycogenosis, or the combination thereof is selected from the group consisting of Sanfilippo syndrome type A, Sanfilippo syndrome type B, Hurler syndrome, Tay-Sachs disease, Gaucher disease, Fabry disease, Pompe disease and Niemann-Pick disease type A/B.

* * * * *